United States Patent
Zhang et al.

(10) Patent No.: US 9,491,944 B2
(45) Date of Patent: Nov. 15, 2016

(54) PESTICIDAL COMPOSITIONS AND RELATED METHODS

(71) Applicant: DOW AGROSCIENCES LLC, Indianapolis, IN (US)

(72) Inventors: Yu Zhang, Carmel, IN (US); Tony K. Trullinger, Westfield, IN (US); Ricky Hunter, Westfield, IN (US); Ann M. Buysse, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 56 days.

(21) Appl. No.: 14/517,619

(22) Filed: Oct. 17, 2014

(65) Prior Publication Data

US 2015/0111735 A1   Apr. 23, 2015

Related U.S. Application Data

(60) Provisional application No. 61/894,348, filed on Oct. 22, 2013.

(51) Int. Cl.
 *A01N 43/647* (2006.01)
 *C07D 401/04* (2006.01)
 *C07D 401/14* (2006.01)

(52) U.S. Cl.
 CPC .......... *A01N 43/647* (2013.01); *C07D 401/04* (2013.01); *C07D 401/14* (2013.01)

(58) Field of Classification Search
 CPC . A01N 43/647; C07D 401/04; C07D 401/14
 See application file for complete search history.

(56) References Cited

U.S. PATENT DOCUMENTS

| | | | |
|---|---|---|---|
| 4,080,457 A | 3/1978 | Harrison et al. | |
| 4,260,765 A | 4/1981 | Harrison et al. | |
| 4,474,599 A * | 10/1984 | Rogers ................. | A01N 43/647 504/230 |
| 4,536,506 A | 8/1985 | Marcoux et al. | |
| 5,625,074 A | 4/1997 | Daum et al. | |
| 5,631,380 A | 5/1997 | Haas et al. | |
| 5,652,372 A | 7/1997 | Muller et al. | |
| 5,693,657 A | 12/1997 | Lee et al. | |
| 5,750,718 A | 5/1998 | Muller et al. | |
| 5,817,677 A | 10/1998 | Linz et al. | |
| 5,854,264 A | 12/1998 | Anthony et al. | |
| 5,854,265 A | 12/1998 | Anthony | |
| 5,869,681 A | 2/1999 | Muller et al. | |
| 6,218,418 B1 | 4/2001 | Pevarello et al. | |
| 6,274,536 B1 | 8/2001 | Nebel et al. | |
| 6,548,525 B2 | 4/2003 | Galemmo, Jr. et al. | |
| 6,720,427 B2 | 4/2004 | Sanner et al. | |
| 6,878,196 B2 | 4/2005 | Harada et al. | |
| 6,916,927 B2 | 7/2005 | Bunnage et al. | |
| 7,192,906 B2 | 3/2007 | Hirohara et al. | |
| 7,196,104 B2 | 3/2007 | Askew, Jr. et al. | |
| 7,319,108 B2 | 1/2008 | Schwink et al. | |
| 7,774,978 B2 | 8/2010 | Ding et al. | |
| 7,803,832 B2 | 9/2010 | Critcher et al. | |
| 7,910,606 B2 | 3/2011 | Nazare et al. | |
| 7,923,573 B2 | 4/2011 | Tamaki et al. | |
| 8,163,756 B2 | 4/2012 | Flynn et al. | |
| 8,198,308 B2 | 6/2012 | Steurer et al. | |
| 8,222,280 B2 | 7/2012 | Liu et al. | |
| 8,350,044 B2 | 1/2013 | Trullinger | |
| 8,664,229 B2 | 3/2014 | Bretschneider | |
| 8,815,271 B2 * | 8/2014 | Yap ....................... | A61K 45/06 424/417 |
| 8,853,246 B2 | 10/2014 | Trullinger | |
| 9,006,446 B2 | 4/2015 | Trullinger | |
| 9,137,998 B2 | 9/2015 | Niyaz | |
| 2002/0013326 A1 | 1/2002 | Tiebes et al. | |
| 2003/0153464 A1 | 8/2003 | Nakamura et al. | |
| 2003/0213405 A1 | 11/2003 | Harada et al. | |
| 2004/0082629 A1 | 4/2004 | Iwataki et al. | |
| 2005/0038059 A1 | 2/2005 | Mueller et al. | |

(Continued)

FOREIGN PATENT DOCUMENTS

| | | |
|---|---|---|
| EP | 0097323 | 1/1984 |
| EP | 0205024 | 12/1986 |
| EP | 0248315 | 12/1987 |
| EP | 0425948 | 5/1991 |
| EP | 1273582 | 1/2003 |
| EP | 1321463 | 6/2003 |
| EP | 1329160 | 7/2003 |
| JP | 153273 | 7/1987 |
| JP | 174905 | 7/1988 |
| JP | 226815 | 9/1989 |

(Continued)

OTHER PUBLICATIONS

PCT International Search Report; PCT/US2014/061078; dated Jan. 15, 2015.
PCT Written Opinion; PCT/US2014/061078; dated Jan. 15, 2015.

*Primary Examiner* — Jane C Oswecki
(74) *Attorney, Agent, or Firm* — Carl D. Corvin; Magelby Cataxinos & Greenwood

(57) ABSTRACT

A pesticidal composition comprises a pyridine triazole compound of formula I or any agriculturally acceptable salt thereof, wherein $R_1$, $R_2$, $R_3$, $R_4$, $R_5$, Z, and x are as described herein. A method of controlling pests comprises applying the pesticidal composition near a population of pests.

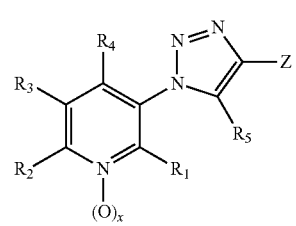

I

38 Claims, No Drawings

(56) References Cited

U.S. PATENT DOCUMENTS

| | | |
|---|---|---|
| 2005/0176710 A1 | 8/2005 | Schwink et al. |
| 2006/0160857 A1 | 7/2006 | Buettelmann et al. |
| 2006/0160875 A1 | 7/2006 | Gaines et al. |
| 2007/0167426 A1 | 7/2007 | Siddiqui et al. |
| 2008/0004301 A1 | 1/2008 | Tamaki et al. |
| 2008/0027046 A1 | 1/2008 | Annan et al. |
| 2009/0069288 A1 | 3/2009 | Breinlinger et al. |
| 2009/0137524 A1 | 5/2009 | Billen et al. |
| 2009/0325956 A1 | 12/2009 | Taniguchi et al. |
| 2010/0130474 A1 | 5/2010 | Bothmann et al. |
| 2010/0204164 A1 | 8/2010 | Crouse et al. |
| 2010/0222320 A1 | 9/2010 | Fischer et al. |
| 2010/0292253 A1 | 11/2010 | Trullinger et al. |
| 2010/0305200 A1 | 12/2010 | Velicelebi et al. |
| 2011/0021771 A1 | 1/2011 | Mallais et al. |
| 2011/0098287 A1 | 4/2011 | Bretschneider et al. |
| 2011/0118290 A1 | 5/2011 | Bretschneider et al. |
| 2011/0166129 A1 | 7/2011 | Machacek et al. |
| 2011/0166143 A1 | 7/2011 | Bretschneider et al. |
| 2011/0184188 A1 | 7/2011 | Wada et al. |
| 2011/0201649 A1 | 8/2011 | Matsuzaki et al. |
| 2011/0212949 A1 | 9/2011 | Bretschneider et al. |
| 2011/0212999 A1 | 9/2011 | Dahl et al. |
| 2011/0275583 A1 | 11/2011 | Bretschneider et al. |
| 2011/0319428 A1 | 12/2011 | Fu Lein et al. |
| 2012/0053146 A1 | 3/2012 | Parker et al. |
| 2012/0094837 A1 | 4/2012 | Muhlthau et al. |
| 2012/0095023 A1 | 4/2012 | Bretschneider et al. |
| 2012/0110701 A1 | 5/2012 | Garizi et al. |
| 2012/0110702 A1 | 5/2012 | Yap et al. |
| 2012/0115811 A1 | 5/2012 | Du et al. |
| 2012/0165345 A1 | 6/2012 | Bretschneider et al. |
| 2012/0220453 A1 | 8/2012 | Lowe et al. |
| 2013/0072382 A1 | 3/2013 | Trullinger et al. |
| 2013/0089622 A1 | 4/2013 | Trullinger et al. |
| 2013/0109566 A1 | 5/2013 | Niyaz et al. |
| 2013/0261141 A1* | 10/2013 | Bretschneider ...... C07D 401/04 514/275 |
| 2013/0288893 A1 | 10/2013 | Buysse et al. |
| 2013/0291227 A1 | 10/2013 | Buysse et al. |
| 2013/0324736 A1 | 12/2013 | Ross, Jr. et al. |
| 2013/0324737 A1 | 12/2013 | Ross, Jr. et al. |
| 2015/0045218 A1 | 2/2015 | Trullinger |
| 2015/0166531 A1* | 6/2015 | Yap .................. A61K 45/06 504/100 |

FOREIGN PATENT DOCUMENTS

| | | |
|---|---|---|
| JP | 03212864 | 7/2003 |
| JP | 2004051628 | 2/2004 |
| JP | 2004292703 | 10/2004 |
| JP | 2012188418 | 10/2012 |
| JP | 2013075871 | 4/2013 |
| JP | 2013082699 | 5/2013 |
| JP | 2013082704 | 5/2013 |
| JP | 2013107867 | 6/2013 |
| JP | 2013129651 | 7/2013 |
| JP | 2013129653 | 7/2013 |
| WO | 9413644 | 6/1994 |
| WO | 9736897 | 10/1997 |
| WO | 9821199 | 5/1998 |
| WO | 9849166 | 11/1998 |
| WO | 0035919 | 6/2000 |
| WO | 0134127 | 5/2001 |
| WO | 0190078 | 11/2001 |
| WO | 02083111 | 10/2002 |
| WO | 03008405 | 1/2003 |
| WO | 03072102 | 9/2003 |
| WO | 2004041813 | 5/2004 |
| WO | 2005070925 | 8/2005 |
| WO | 2005074875 | 8/2005 |
| WO | 2006023462 | 3/2006 |
| WO | 2006033005 | 3/2006 |
| WO | 2006046593 | 5/2006 |
| WO | 2006103045 | 10/2006 |
| WO | 2007005838 | 1/2007 |
| WO | 2007087427 | 8/2007 |
| WO | 2007098826 | 9/2007 |
| WO | 2008005457 | 1/2008 |
| WO | 2008079277 | 7/2008 |
| WO | 2008090382 | 7/2008 |
| WO | 2008100426 | 8/2008 |
| WO | 2009149858 | 12/2009 |
| WO | 2010006713 | 1/2010 |
| WO | 2010009290 | 1/2010 |
| WO | 2010012442 | 2/2010 |
| WO | 2010033360 | 3/2010 |
| WO | 2010048207 | 4/2010 |
| WO | 2010060379 | 6/2010 |
| WO | 2010075376 | 7/2010 |
| WO | 2010129497 | 11/2010 |
| WO | 2010133336 | 11/2010 |
| WO | 2010146236 | 12/2010 |
| WO | 2011003065 | 1/2011 |
| WO | 2011043371 | 4/2011 |
| WO | 2011045224 | 4/2011 |
| WO | 2011045240 | 4/2011 |
| WO | 2011091153 | 7/2011 |
| WO | 2011101229 | 8/2011 |
| WO | 2011126903 | 10/2011 |
| WO | 2011128304 | 10/2011 |
| WO | 2011134964 | 11/2011 |
| WO | 2011138285 | 11/2011 |
| WO | 2011163518 | 12/2011 |
| WO | 2012000896 | 1/2012 |
| WO | 2012004217 | 1/2012 |
| WO | 2012007500 | 1/2012 |
| WO | 2012035011 | 3/2012 |
| WO | 2012052412 | 4/2012 |
| WO | 2012061290 | 5/2012 |
| WO | 2012070114 | 5/2012 |
| WO | 2012102387 | 8/2012 |
| WO | 2012108511 | 8/2012 |
| WO | 2012168361 | 12/2012 |
| WO | 2012175474 | 12/2012 |
| WO | 2013000931 | 1/2013 |
| WO | 2013001094 | 1/2013 |
| WO | 2013010946 | 1/2013 |
| WO | 2013062980 | 5/2013 |
| WO | 2013156431 | 10/2013 |
| WO | 2013156433 | 10/2013 |
| WO | 2013162715 | 10/2013 |
| WO | 2013162716 | 10/2013 |

* cited by examiner

PESTICIDAL COMPOSITIONS AND RELATED METHODS

CROSS REFERENCE TO RELATED APPLICATION

This application claims the benefit of U.S. Provisional Patent Application Ser. No. 61/894,348, filed Oct. 22, 2013, the disclosure of which is hereby incorporated herein in its entirety by this reference.

TECHNICAL FIELD

This disclosure relates to the field of compounds having pesticidal utility against pests in Phyla Nematoda, Arthropoda, and/or Mollusca, processes to produce such compounds and intermediates used in such processes. These compounds may be used, for example, as nematicides, acaricides, insecticides, miticides, and/or molluscicides.

BACKGROUND

Controlling pest populations is essential to human health, modern agriculture, food storage, and hygiene. There are more than ten thousand species of pests that cause losses in agriculture and the world-wide agricultural losses amount to billions of U.S. dollars each year. Accordingly, there exists a continuous need for new pesticides and for methods of producing and using such pesticides.

DISCLOSURE

Definitions

The examples given in the definitions are non-exhaustive and must not be construed as limiting the present disclosure. It is understood that a substituent should comply with chemical bonding rules and steric compatibility constraints in relation to the particular molecule to which it is attached.

"Alkyl" means and includes an acyclic, saturated, branched or unbranched hydrocarbon. Non-limiting examples may include methyl, ethyl, propyl, isopropyl, 1-butyl, 2-butyl, isobutyl, tert-butyl, pentyl, 2-methylbutyl, 1,1-dimethylpropyl, hexyl, heptyl, octyl, nonyl, or decyl.

"Cycloalkyl" means and includes a monocyclic or polycyclic saturated hydrocarbon. Non-limiting examples may include cyclopropyl, cyclobutyl, cyclopentyl, cyclohexyl, cycloheptyl, cyclooctyl, cyclodecyl, norbornyl, bicycle [2.2.2]octyl, or decahydronapthyl.

"Alkenyl" means and includes an acyclic, branched or unbranched hydrocarbon containing at least one carbon-carbon double bond. Non-limiting examples may include ethenyl, propenyl, butenyl, pentenyl, hexenyl, heptenyl, octenyl, nonenyl, or decenyl.

"Cycloalkenyl" means and includes a monocyclic or polycyclic hydrocarbon containing at least one carbon-carbon double bond. Non-limiting examples may include cyclopentenyl, cyclohexenyl, cycloheptenyl, cyclooctenyl, or cyclodecenyl.

"Alkynyl" means and includes acyclic, branched or unbranched hydrocarbon containing at least one carbon-carbon triple bond. Non-limiting examples may include ethynyl, propargyl, butynyl, pentynyl, hexynyl, heptynyl, octynyl, nonynyl, or decynyl.

"Cycloalkynyl" means and includes a monocyclic or polycyclic hydrocarbon containing at least one carbon-carbon triple bond. Non-limiting examples may include cycloheptynyl, cyclooctynyl, or cyclodecynyl.

"Aryl" means and includes an aromatic compound with or without any substitution. Non-limiting examples may include phenyl or naphthyl.

"Alkoxy" means and includes an alkyl group containing at least one carbon-oxygen single bond. Non-limiting examples may include methoxy, ethoxy, propoxy, butoxy, cyclopropoxy, cyclobutoxy, or cyclopentoxy.

"Alkenyloxy" means and includes an alkenyl containing at least one carbon-oxygen single bond. Non-limiting examples may include allyloxy, butenyloxy, pentenyloxy, hexenyloxy, heptenyloxy, octenyloxy, nonenyloxy, or decenyloxy "Alkynyloxy" means and includes an alkynyl containing at least one carbon-oxygen single bond. Non-limiting examples may include pentynyloxy, hexynyloxy, heptynyloxy, octynyloxy, nonynyloxy, or decynyloxy.

"Cycloalkoxy" means and includes a cycloalkyl containing at least one carbon-oxygen single bond. Non-limiting examples may include cyclopropyloxy, cyclobutyloxy, cyclopentyloxy, cyclohexyloxy, cycloheptyloxy, cyclooctyloxy, cyclodecyloxy, norbornyloxy, or bicyclo[2.2.2]octyloxy.

"Cyclohaloalkyl" means and includes a monocyclic or polycyclic, saturated substituent comprising carbon, halogen, and hydrogen. Non-limiting examples may include 1-chlorocyclopropyl, 1-chlorocyclobutyl, or 1-dichlorocyclopentyl.

"Cycloalkenyloxy" means and include a cycloalkenyl further consisting of a carbon-oxygen single bond. Non-limiting examples may include cyclobutenyloxy, cyclopentenyloxy, cyclohexenyloxy, cycloheptenyloxy, cyclooctenyloxy, cyclodecenyloxy, norbornenyloxy, or bicyclo[2.2.2]octenyloxy.

"Alkylthio" means and includes an alkyl group containing at least one carbon-sulfur single bond.

"Haloalkylthio" means and includes an alkyl group containing at least one carbon-sulfur single bond and halogen atom.

"Halo" or "halogen" means and includes fluorine, chlorine, bromine, or iodine.

"Haloalkyl" means and includes an alkyl group substituted with at least one halogen atom.

"Haloalkoxy" means and includes an alkoxy group substituted with at least one halogen atom.

"Heteroatom" means and includes sulfur (S), oxygen (O), or nitrogen (N) atom.

"Heteroalkyl" means and includes an alkyl containing at least one sulfur (S), oxygen (O), or nitrogen (N) atom.

"Heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen. In the case of sulfur, that atom can be in other oxidation states such as a sulfoxide and sulfone. Examples of aromatic heterocyclyls include, but are not limited to, benzofuranyl, benzoisothiazolyl, benzoisoxazolyl, benzoxazolyl, benzothienyl, benzothiazolyl, cinnolinyl, furanyl, imidazolyl, indazolyl, indolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, and triazolyl. Examples of fully saturated heterocyclyls include, but are not limited to, piperazinyl, piperidinyl, morpholinyl, pyrrolidinyl, oxetanyl, tetrahydrofuranyl, tetrahydrothienyl and tetrahydropyranyl. Examples of partially unsaturated heterocyclyls include, but are not limited to, 1,2,3,4-tetrahydroquinolinyl, 4,5-dihydro-oxazolyl, 4,5-dihydro-1H-pyrazolyl, 4,5-dihydro-isoxazolyl, and 2,3-dihydro-[1,3,4]-oxadiazolyl. Additional examples include the following:

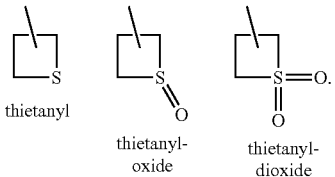

"Pesticidally effective amount" means and includes an amount of active material that causes an adverse effect to the at least one insect, wherein the adverse effect may include deviations from natural development, killing, regulation, or the like.

"Control" or grammatical variations thereof means and includes regulating the number of living insects or regulating the number of viable eggs of the insects.

"Synergistic effect" or grammatical variations thereof means and includes a cooperative action encountered in a combination of two or more active agents in which the combined activity of the two or more active agents exceeds the sum of the activity of each active agent alone.

Pesticidal Compounds

In one particular embodiment, a pesticidal composition comprises a pyridine triazole compounds of formula I, or any agriculturally acceptable salt thereof:

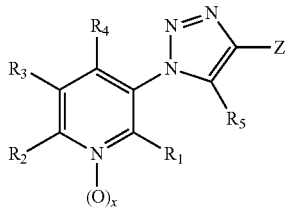

wherein:

$R_1$, $R_2$, and $R_4$ are independently selected from hydrogen, F, Cl, Br, I, substituted or unsubstituted $C_1$-$C_6$ alkyl, or substituted or unsubstituted $C_1$-$C_6$ haloalkyl, wherein each $R_1$, $R_2$, and $R_4$, when substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_3$-$C_{10}$ cycloalkyl, or $C_3$-$C_{10}$ halocycloalkyl where each of which may be unsubstituted or substituted with $R_{11}$;

$R_3$ is selected from hydrogen, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_3$-$C_{10}$ cycloalkyl, substituted or unsubstituted $C_1$-$C_6$ haloalkyl, substituted or unsubstituted $C_6$-$C_{20}$ aryl, substituted or unsubstituted $C_1$-$C_{20}$ heterocyclyl, $OR_{11}$, $C(=X_1)R_{11}$, $C(=X_1)OR_{11}$, $C(=X_1)N(R_{11})_2$, $N(R_{11})_2$, $N(R_{11})C(=X_1)R_{11}$, $SR_{11}$, $S(O)_nOR_{11}$, or $R_{11}S(O)_nR_{11}$, wherein $R_3$, when substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, $OR_{11}$, $S(O)_nOR_{11}$, $C_6$-$C_{20}$ aryl, or $C_1$-$C_{20}$ heterocyclyl, wherein each of which may be unsubstituted or substituted with $R_{11}$;

$R_5$ is selected from hydrogen, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, $C_3$-$C_{10}$ cycloalkyl, substituted or unsubstituted $C_6$-$C_{20}$ aryl, substituted or unsubstituted $C_1$-$C_{20}$ heterocyclyl, $OR_{11}$, $C(=X_1)R_{11}$, $C(=X_1)OR_{11}$, $C(=X_1)N(R_{11})_2$, $N(R_{11})_2$, $N(R_{11})C(=X_1)R_{11}$, $SR_{11}$, $S(O)_nOR_{11}$, or $R_{11}S(O)_nR_{11}$, wherein $R_5$, when substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, $OR_{11}$, $S(O)_nOR_{11}$, $C_6$-$C_{20}$ aryl, or $C_1$-$C_{20}$ heterocyclyl, wherein each of which may be unsubstituted or substituted with $R_{11}$;

Z is $Z_1$, $Z_2$, $Z_3$, $Z_4$, $Z_5$, $Z_6$, $Z_7$ or $Z_8$;

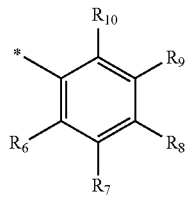

$Z_1$

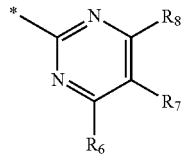

$Z_2$

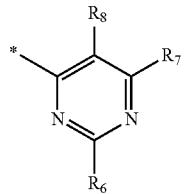

$Z_3$

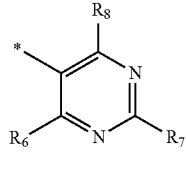

$Z_4$

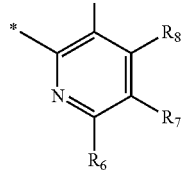

$Z_5$

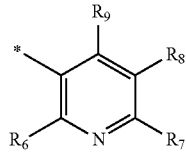

$Z_6$

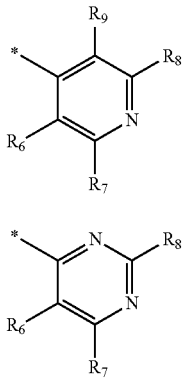

R₆ is selected from hydrogen, F, Cl, Br, I, CN, NO₂, OR₁₁, substituted or unsubstituted C₁-C₆ alkyl, substituted or unsubstituted C₂-C₆ alkenyl, substituted or unsubstituted C₁-C₆ alkoxy, substituted or unsubstituted C₃-C₁₀ cycloalkyl, substituted or unsubstituted C₃-C₁₀ halocycloalkyl substituted or unsubstituted C₃-C₁₀ cycloalkenyl, substituted or unsubstituted C₆-C₂₀ aryl, substituted or unsubstituted C₁-C₂₀ heterocyclyl, C(=X₁)R₁₁, C(=X₁)OR₁₁, C(=X₁)N(R₁₁)₂, N(R₁₁)₂, N(R₁₁)C(=X₁)R₁₁, SR₁₁, S(O)ₙOR₁₁, or R₁₁S(O)ₙR₁₁, wherein R6, when substituted, has one or more substituents selected from F, Cl, Br, I, CN, NO₂, C₁-C₆ alkyl, C₂-C₆ alkenyl, C₁-C₆ haloalkyl, C₂-C₆ haloalkenyl, C₁-C₆ haloalkyloxy, C₂-C₆ haloalkenyloxy, C₃-C₁₀ cycloalkyl, C₃-C₁₀ cycloalkenyl, C₃-C₁₀ halocycloalkyl, C₃-C₁₀ halocycloalkenyl, oxo, OR₁₁, S(O)ₙR₁₁, C₆-C₂₀ aryl, or C₁-C₂₀ heterocyclyl, wherein each of which may be unsubstituted or substituted with R₁₁;

R₇ is selected from hydrogen, F, Cl, Br, I, CN, NO₂, OR₁₁, substituted or unsubstituted C₁-C₆ alkyl, substituted or unsubstituted C₂-C₆ alkenyl, substituted or unsubstituted C₁-C₆ alkoxy, substituted or unsubstituted C₃-C₁₀ cycloalkyl, substituted or unsubstituted C₃-C₁₀ halocycloalkyl substituted or unsubstituted C₃-C₁₀ cycloalkenyl, substituted or unsubstituted C₆-C₂₀ aryl, substituted or unsubstituted C₁-C₂₀ heterocyclyl, C(=X₁)R₁₁, C(=X₁)OR₁₁, C(=X₁)N(R₁₁)₂, N(R₁₁)₂, N(R₁₁)C(=X₁)R₁₁, SR₁₁, S(O)ₙOR₁₁, or R₁₁S(O)ₙR₁₁, wherein R₇, when substituted, has one or more substituents selected from F, Cl, Br, I, CN, NO₂, C₁-C₆ alkyl, C₂-C₆ alkenyl, C₁-C₆ haloalkyl, C₂-C₆ haloalkenyl, C₁-C₆ haloalkyloxy, C₂-C₆ haloalkenyloxy, C₃-C₁₀ cycloalkyl, C₃-C₁₀ cycloalkenyl, C₃-C₁₀ halocycloalkyl, C₃-C₁₀ halocycloalkenyl, oxo, OR₁₁, S(O)ₙR₁₁, C₆-C₂₀ aryl, or C₁-C₂₀ heterocyclyl, wherein each of which may be unsubstituted or substituted with R₁₁;

R₈ is selected from hydrogen, F, Cl, Br, I, CN, NO₂, OR₁₁, substituted or unsubstituted C₁-C₆ alkyl, substituted or unsubstituted C₂-C₆ alkenyl, substituted or unsubstituted C₁-C₆ alkoxy, substituted or unsubstituted C₃-C₁₀ cycloalkyl, substituted or unsubstituted C₃-C₁₀ halocycloalkyl substituted or unsubstituted C₃-C₁₀ cycloalkenyl, substituted or unsubstituted C₆-C₂₀ aryl, substituted or unsubstituted C₁-C₂₀ heterocyclyl, C(=X₁)R₁₁, C(=X₁)OR₁₁, C(=X₁)N(R₁₁)₂, N(R₁₁)₂, N(R₁₁)C(=X₁)R₁₁, SR₁₁, S(O)ₙOR₁₁, or R₁₁S(O)ₙR₁₁, wherein R₈, when substituted, has one or more substituents selected from F, Cl, Br, I, CN, NO₂, C₁-C₆ alkyl, C₂-C₆ alkenyl, C₁-C₆ haloalkyl, C₂-C₆ haloalkenyl, C₁-C₆ haloalkyloxy, C₂-C₆ haloalkenyloxy, C₃-C₁₀ cycloalkyl, C₃-C₁₀ cycloalkenyl, C₃-C₁₀ halocycloalkyl, C₃-C₁₀ halocycloalkenyl, oxo, OR₁₁, S(O)ₙR₁₁, C₆-C₂₀ aryl, or C₁-C₂₀ heterocyclyl, wherein each of which may be unsubstituted or substituted with R₁₁;

R₉ is selected from hydrogen, F, Cl, Br, I, CN, NO₂, —OR₁₁, substituted or unsubstituted C₁-C₆ alkyl, substituted or unsubstituted C₂-C₆ alkenyl, substituted or unsubstituted C₁-C₆ alkoxy, substituted or unsubstituted C₃-C₁₀ cycloalkyl, substituted or unsubstituted C₃-C₁₀ halocycloalkyl, substituted or unsubstituted C₃-C₁₀ cycloalkenyl, substituted or unsubstituted C₆-C₂₀ aryl, substituted or unsubstituted C₁-C₂₀ heterocyclyl, C(=X₁)R₁₁, C(=X₁)OR₁₁, C(=X₁)N(R₁₁)₂, N(R₁₁)₂, N(R₁₁)C(=X₁)R₁₁, SR₁₁, S(O)ₙOR₁₁, or R₁₁S(O)ₙR₁₁, wherein R₉, when substituted, has one or more substituents selected from F, Cl, Br, I, CN, NO₂, C₁-C₆ alkyl, C₂-C₆ alkenyl, C₁-C₆ haloalkyl, C₂-C₆ haloalkenyl, C₁-C₆ haloalkyloxy, C₂-C₆ haloalkenyloxy, C₃-C₁₀ cycloalkyl, C₃-C₁₀ cycloalkenyl, C₃-C₁₀ halocycloalkyl, C₃-C₁₀ halocycloalkenyl, oxo, OR₁₁, S(O)ₙR₁₁, C₆-C₂₀ aryl, or C₁-C₂₀ heterocyclyl, wherein each of which may be unsubstituted or substituted with R₁₁;

R₁₀ is selected from hydrogen, F, Cl, Br, I, CN, NO₂, OR₁₁, substituted or unsubstituted C₁-C₆ alkyl, substituted or unsubstituted C₂-C₆ alkenyl, substituted or unsubstituted C₁-C₆ alkoxy, substituted or unsubstituted C₃-C₁₀ cycloalkyl, substituted or unsubstituted C₃-C₁₀ halocycloalkyl substituted or unsubstituted C₃-C₁₀ cycloalkenyl, substituted or unsubstituted C₆-C₂₀ aryl, substituted or unsubstituted C₁-C₂₀ heterocyclyl, C(=X₁)R₁₁, C(=X₁)OR₁₁, C(=X₁)N(R₁₁)₂, N(R₁₁)₂, N(R₁₁)C(=X₁)R₁₁, SR₁₁, S(O)ₙOR₁₁, or R₁₁S(O)ₙR₁₁, wherein R₁₀, when substituted, has one or more substituents selected from F, Cl, Br, I, CN, NO₂, C₁-C₆ alkyl, C₂-C₆ alkenyl, C₁-C₆ haloalkyl, C₂-C₆ haloalkenyl, C₁-C₆ haloalkyloxy, C₂-C₆ haloalkenyloxy, C₃-C₁₀ cycloalkyl, C₃-C₁₀ cycloalkenyl, C₃-C₁₀ halocycloalkyl, C₃-C₁₀ halocycloalkenyl, oxo, OR₁₁, S(O)ₙR₁₁, C₆-C₂₀ aryl, or C₁-C₂₀ heterocyclyl, wherein each of which may be unsubstituted or substituted with R₁₁;

R₁₁ is selected from hydrogen, F, Cl, Br, I, CN, NO₂, substituted or unsubstituted C₁-C₆ alkyl, substituted or unsubstituted C₂-C₆ alkenyl, substituted or unsubstituted C₁-C₆ alkoxy, substituted or unsubstituted C₂-C₆ alkenyloxy, substituted or unsubstituted C₃-C₁₀ cycloalkyl, substituted or unsubstituted C₃-C₁₀ cycloalkenyl, substituted or unsubstituted C₆-C₂₀ aryl, substituted or unsubstituted C₁-C₂₀ heterocyclyl, substituted or unsubstituted S(O)ₙC₁-C₆ alkyl, or substituted or unsubstituted N(C₁-C₆ alkyl)₂, wherein R₁₁, when substituted, has one or more substituents selected from F, Cl, Br, I, CN, NO₂, C₁-C₆ alkyl, C₂-C₆ alkenyl, C₁-C₆ haloalkyl, C₂-C₆ haloalkenyl, C₁-C₆ haloalkyloxy, C₂-C₆ haloalkenyloxy, C₃-C₁₀ cycloalkyl, C₃-C₁₀ cycloalkenyl, C₃-C₁₀ halocycloalkyl, C₃-C₁₀ halocycloalkenyl, OC₁-C₆ alkyl, OC₁-C₆ haloalkyl, S(O)ₙC₁-C₆alkyl, S(O)ₙOC₁-C₆ alkyl, C₆-C₂₀ aryl, or C₁-C₂₀ heterocyclyl;

X₁=O or S;

n is 0, 1, or 2; and x is 0 or 1.

In another embodiment, and in any combination with any of the previous or following embodiments, R₁, R₂, and R₄ are H.

In another embodiment, and in any combination with any of the previous or following embodiments, R₃ is selected from H, F, Cl, Br, or I, preferably, H or F.

In another embodiment, and in any combination with any of the previous or following embodiments, R₅ is hydrogen.

In another embodiment, and in any combination with any of the previous or following embodiments, Z is Z₅.

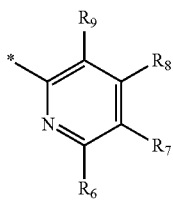

In another embodiment, and in any combination with any of the previous or following embodiments, $R_6$ and $R_7$ are independently selected from hydrogen, substituted or unsubstituted $C_1$-$C_6$ haloalkyl and $R_8$ and $R_9$ are hydrogen.

While some embodiments have been described herein, other embodiments and combinations of the described embodiments with other embodiments may be possible.

In one embodiment, the pyridine triazole compounds of formula I may be prepared, as shown in Scheme 1, by reacting the triazole compound 1-1 (prepared as described in *Bioorganic & Medicinal Chemistry* 2008, 16, 9817) with an aryl/heterocyclic halide 1-2 in the presence of a catalyst and a base in a polar aprotic solvent such as dioxane, at a temperature of from about −78° C. to about 120° C. Non-limiting examples of the catalysts may include bis-(triphenylphosphine) palladium (II) dichloride ($Pd(PPh_3)_2Cl_2$) and copper(I) iodide (CuI). Non-limiting examples of the base may include a salt such as cesium fluoride (CsF).

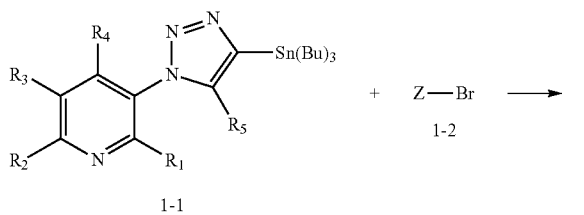

Scheme 1

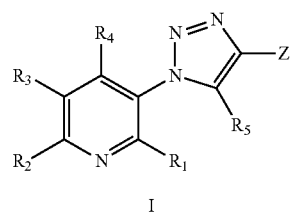

In another embodiment, the pyridine triazole compounds of formula I may be prepared, as shown in Scheme 2, by reacting 4-iodo-triazole compound 2-1 (prepared as described in *Bioorganic & Medicinal Chemistry* 2008, 16, 9817) with an aryl/heterocyclic boronic acid compound (2-2) in the presence of a catalyst and a base in a suitable solvent system, such as a mixture of 1,4-dioxane and water, at a temperature of from about 25° C. to about 120° C. Non-limiting examples of the catalyst may include $Pd(PPh_3)_2Cl_2$ and non-limiting examples of the base may include sodium carbonate ($Na_2CO_3$).

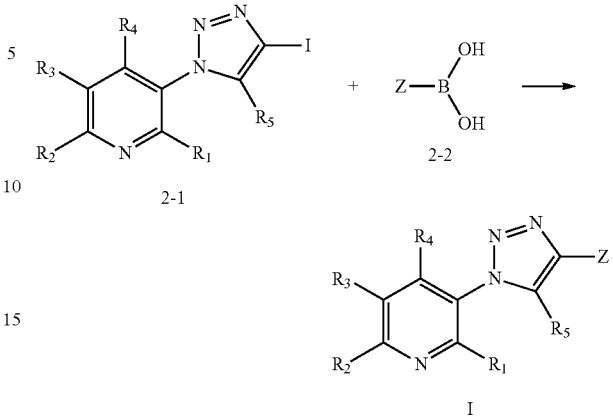

Scheme 2

Pesticidally Acceptable Acid Addition Salts, Salt Derivatives, Solvates, Ester Derivatives, Polymorphs, Isotopes, Radionuclides and Stereoisomers In some embodiments, the pyridine triazole compounds of formula I may be formulated into pesticidally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, hydroxyethanesulfonic, and trifluoroacetic acids. Additionally, by way of a non-limiting example, an acid function can form salts including those derived from alkali or alkaline earth metals and those derived from ammonia and amines. Examples of preferred cations include sodium, potassium, and magnesium.

In some embodiments, the pyridine triazole compounds of formula I may be formulated into salt derivatives. By way of a non-limiting example, a salt derivative can be prepared by contacting a free base with a sufficient amount of the desired acid to produce a salt. A free base may be regenerated by treating the salt with a suitable dilute aqueous base solution such as dilute aqueous sodium hydroxide (NaOH), potassium carbonate, ammonia, and sodium bicarbonate. As an example, in many cases, a pesticide, such as 2,4-D, is made more water-soluble by converting it to its dimethylamine salt.

In further embodiments, the pyridine triazole compounds of formula I may be formulated into stable complexes with a solvent, such that the complex remains intact after the non-complexed solvent is removed. These complexes are often referred to as "solvates." However, it is particularly desirable to form stable hydrates with water as the solvent.

In some embodiments, the pyridine triazole compounds of formula I may be made into ester derivatives. These ester derivatives can then be applied in the same manner as the invention disclosed in this document is applied.

In some embodiments, the pyridine triazole compounds of formula I may be made as various crystal polymorphs. Polymorphism is important in the development of agrochemicals since different crystal polymorphs or structures of the same molecule can have vastly different physical properties and biological performances.

In further embodiments, the pyridine triazole compounds of formula I may be made with different isotopes. Of particular importance are molecules having $^2H$ (also known as deuterium) in place of $^1H$.

In some embodiments, the pyridine triazole compounds of formula I may be made with different radionuclides. Of particular importance are molecules having $^{13}C$ or $^{14}C$.

In some embodiments, the pyridine triazole compounds of formula I may exist as one or more stereoisomers. Thus, certain molecules can be produced as racemic mixtures. It will be appreciated by those skilled in the art that one stereoisomer may be more active than the other stereoisomers. Individual stereoisomers may be obtained by known selective synthetic procedures, by conventional synthetic procedures using resolved starting materials, or by conventional resolution procedures. Certain molecules disclosed in this document can exist as two or more isomers. The various isomers include geometric isomers, diastereomers, and enantiomers. Thus, the molecules disclosed in this document include geometric isomers, racemic mixtures, individual stereoisomers, and optically active mixtures. It will be appreciated by those skilled in the art that one isomer may be more active than the others. The structures disclosed in the present disclosure are drawn in only one geometric form for clarity, but are intended to represent all geometric forms of the molecule.

Pesticidal Compositions

In one particular embodiment, a pesticidal composition comprises a pyridine triazole compounds of formula I, or any agriculturally acceptable salt thereof In some embodiments, a pesticidal composition comprises a pyridine triazole compounds of formula I or any agriculturally acceptable salt thereof, and a phytologically-acceptable inert carrier (e.g., solid carrier, or liquid carrier).

In one embodiment, the pesticidal composition may further comprise at least one additive selected from surfactant, a stabilizer, an emetic agent, a disintegrating agent, an antifoaming agent, a wetting agent, a dispersing agent, a binding agent, dyes, or fillers.

In some embodiments, the pesticidal compositions may be in the form of solid. Non-limiting examples of the solid forms may include power, dust or granular formulations.

In other embodiments, the pesticidal compositions may be in the form of liquid formulation. Examples of the liquid forms may include, but not limited to, dispersion, suspension, emulsion or solution in appropriate liquid carrier.

In further embodiments, the pesticidal compositions may be in the form of liquid dispersion, wherein the pyridine triazole compounds of formula I may be dispersed in water or other agriculturally suitable liquid carrier.

In yet further embodiments, the pesticidal compositions may be in the form of solution in an appropriate organic solvent. In one embodiment, the spray oils, which are widely used in agricultural chemistry, may be used as an organic solvent for the pesticidal compositions.

The pesticidal composition may be used in conjunction (such as, in a compositional mixture, or a simultaneous or sequential application) with one or more compounds having acaricidal, algicidal, avicidal, bactericidal, fungicidal, herbicidal, insecticidal, molluscicidal, nematicidal, rodenticidal, and/or virucidal properties.

Furthermore, the pesticidal composition may be used in conjunction (such as, in a compositional mixture, or a simultaneous or sequential application) with one or more compounds that are antifeedants, bird repellents, chemosterilants, herbicide safeners, insect attractants, insect repellents, mammal repellents, mating disrupters, plant activators, plant growth regulators, and/or synergists.

Insecticides

Non-limiting examples of insecticides that may be used in combination with the pyridine triazole compounds of formula I may include 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, $\alpha/p/\omega$-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdépalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide (additionally resolved isomers thereof), flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, fufenozide, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hyprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, meperfluthrin, mephosfolan, mercurous chloride, mesulfenfos, metaflumizone, methacrifos, methamidophos, methidathion, methiocarb, methocrotophos, methomyl, methoprene, methothrin, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemetonmethyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, profluthrin, promacyl, promecarb, propaphos, propetamphos, propoxur, prothidathion, prothiofos, prothoate, protrifenbute, pymetrozine, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, Aeto-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, or zolaprofos.

Acaricides

Non-limiting examples of acaricides that may be used in combination with the pyridine triazole compounds of formula I may include acequinocyl, amidoflumet, arsenous oxide, azobenzene, azocyclotin, benomyl, benoxafos, benzoximate, benzyl benzoate, bifenazate, binapacryl, bromopropylate, chinomethionat, chlorbenside, chlorfenethol, chlorfenson, chlorfensulphide, chlorobenzilate, chloromebuform, chloromethiuron, chloropropylate, clofentezine, cyenopyrafen, cyflumetofen, cyhexatin, dichlofluanid, dicofol, dienochlor, diflovidazin, dinobuton, dinocap, dinocap-4, dinocap-6, dinocton, dinopenton, dinosulfon, dinoterbon, diphenyl sulfone, disulfiram, dofenapyn, etoxazole, fenazaquin, fenbutatin oxide, fenothiocarb, fenpyroximate, fenson, fentrifanil, fluacrypyrim, fluazuron, flubenzimine, fluenetil, flumethrin, fluorbenside, hexythiazox, mesulfen, MNAF, nikkomycins, proclonol, propargite, quintiofos, spirodiclofen, sulfiram, sulfur, tetradifon, tetranactin, tetrasul, or thioquinox.

Nematicides

Non-limiting examples of nematicides that may be used in combination with the pyridine triazole compounds of formula I may include 1,3-dichloropropene, benclothiaz, dazomet, dazomet-sodium, DBCP, DCIP, diamidafos, fluensulfone, fosthiazate, furfural, imicyafos, isamidofos, isazofos, metam, metam-ammonium, metam-potassium, metam-sodium, phosphocarb, or thionazin.

Fungicides

Non-limiting examples of fungicides that may be used in combination with the pyridine triazole compounds of formula I may include (3-ethoxypropyl)mercury bromide, 2-methoxyethylmercury chloride, 2-phenylphenol, 8-hydroxyquinoline sulfate, 8-phenylmercurioxyquinoline, acibenzolar, acibenzolar-S-methyl, acypetacs, acypetacs-copper, acypetacs-zinc, aldimorph, allyl alcohol, ametoctradin, amisulbrom, ampropylfos, anilazine, aureofungin, azaconazole, azithiram, azoxystrobin, barium polysulfide, benalaxyl, benalaxyl-M, benodanil, benomyl, benquinox, bentaluron, benthiavalicarb, benthiavalicarb-isopropyl, benzalkonium chloride, benzamacril, benzamacril-isobutyl, benzamorf, benzohydroxamic acid, bethoxazin, binapacryl, biphenyl, bitertanol, bithionol, bixafen, blasticidin-S, Bordeaux mixture, boscalid, bromuconazole, bupirimate, Burgundy mixture, buthiobate, butylamine, calcium polysulfide, captafol, captan, carbamorph, carbendazim, carboxin, carpropamid, carvone, Cheshunt mixture, chinomethionat, chlobenthiazone, chloraniformethan, chloranil, chlorfenazole, chlorodinitronaphthalene, chloroneb, chloropicrin, chlorothalonil, chlorquinox, chlozolinate, climbazole, clotrimazole, copper acetate, copper carbonate, basic, copper hydroxide, copper naphthenate, copper oleate, copper oxychloride, copper silicate, copper sulfate, copper zinc chromate, cresol, cufraneb, cuprobam, cuprous oxide, cyazofamid, cyclafuramid, cycloheximide, cyflufenamid, cymoxanil, cypendazole, cyproconazole, cyprodinil, dazomet, dazomet-sodium, DBCP, debacarb, decafentin, dehydroacetic acid, dichlofluanid, dichlone, dichlorophen, dichlozoline, diclobutrazol, diclocymet, diclomezine, diclomezine-sodium, dicloran, diethofencarb, diethyl pyrocarbonate, difenoconazole, diflumetorim, dimethirimol, dimethomorph, dimoxystrobin, diniconazole, diniconazole-M, dinobuton, dinocap, dinocap-4, dinocap-6, dinocton, dinopenton, dinosulfon, dinoterbon, diphenylamine, dipyrithione, disulfiram, ditalimfos, dithianon, DNOC, DNOC-ammonium, DNOC-potassium, DNOC-sodium, dodemorph, dodemorph acetate, dodemorph benzoate, dodicin, dodicin-sodium, dodine, drazoxolon, edifenphos, epoxiconazole, etaconazole, etem, ethaboxam, ethirimol, ethoxyquin, ethylmercury 2,3-dihydroxypropyl mercaptide, ethylmercury acetate, ethylmercury bromide, ethylmercury chloride, ethylmercury phosphate, etridiazole, famoxadone, fenamidone, fenaminosulf, fenapanil, fenarimol, fenbuconazole, fenfuram, fenhexamid, fenitropan, fenoxanil, fenpiclonil, fenpropidin, fenpropimorph, fentin, fentin chloride, fentin hydroxide, ferbam, ferimzone, fluazinam, fludioxonil, flumetover, flumorph, fluopicolide, fluopyram, fluoroimide, fluotrimazole, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, furcarbanil, furconazole, furconazole-cis, furfural, furmecyclox, furophanate, glyodin, griseofulvin, guazatine, halacrinate, hexachlorobenzene, hexachlorobutadiene, hexaconazole, hexylthiofos, hydrargaphen, hymexazol, imazalil, imazalil nitrate, imazalil sulfate, imibenconazole, iminoctadine, iminoctadine triacetate, iminoctadine trialbesilate, iodomethane, ipconazole, iprobenfos, iprodione, iprovalicarb, isoprothiolane, isopyrazam, isotianil, isovaledione, kasugamycin, kresoxim-methyl, mancopper, mancozeb, mandipropamid, maneb, mebenil, mecarbinzid, mepanipyrim, mepronil, meptyldinocap, mercuric chloride, mercuric oxide, mercurous chloride, metalaxyl, metalaxyl-M, metam, metam-ammonium, metam-potassium, metam-sodium, metazoxolon, metconazole, methasulfocarb, methfuroxam, methyl bromide, methyl isothiocyanate, methylmercury benzoate, methylmercury dicyandiamide, methylmercury pentachlorophenoxide, metiram, metominostrobin, metrafenone, metsulfovax, milneb, myclobutanil, myclozolin, N-(ethylmercury)-p-toluenesulphonanilide, nabam, natamycin, nitrostyrene, nitrothal-isopropyl, nuarimol, OCH, octhilinone, ofurace, orysastrobin, oxadixyl, oxine-copper, oxpoconazole, oxpoconazole fumarate, oxycarboxin, pefurazoate, penconazole, pencycuron, penflufen, pentachlorophenol, penthiopyrad, phenylmercuriurea, phenylmercury acetate, phenylmercury chloride, phenylmercury derivative of pyrocatechol, phenylmercury nitrate, phenylmercury salicylate, phosdiphen, phthalide, picoxystrobin, piperalin, polycarbamate, polyoxins, polyoxorim, polyoxorim-zinc, potassium azide, potassium polysulfide, potassium thiocyanate, probenazole, prochloraz, procymidone, propamocarb, propamocarb hydrochloride, propiconazole, propineb, proquinazid, prothiocarb, prothiocarb hydrochloride, prothioconazole, pyracarbolid, pyraclostrobin, pyraclostrobin, pyrametostrobin, pyraoxystrobin, pyrazophos, pyribencarb, pyridinitril, pyrifenox, pyrimethanil, pyriofenone, pyroquilon, pyroxychlor, pyroxyfur, quinacetol, quinacetol sulfate, quinazamid, quinconazole, quinoxyfen, quintozene, rabenzazole, salicylanilide, sedaxane, silthiofam, simeconazole, sodium azide, sodium orthophenylphenoxide, sodium pentachlorophenoxide, sodium polysulfide, spiroxamine, streptomycin, sulfur, sultropen, TCMTB, tebuconazole, tebufloquin, tecloftalam, tecnazene, tecoram, tetraconazole, thiabendazole, thiadifluor, thicyofen, thifluzamide, thiochlorfenphim, thiomersal, thiophanate, thiophanate-methyl, thioquinox, thiram, tiadinil, tioxymid, tolclofos-methyl, tolylfluanid, tolylmercury acetate, triadimefon, triadimenol, triamiphos, triarimol, triazbutil, triazoxide, tributyltin oxide, trichlamide, tricyclazole, tridemorph, trifloxystrobin, triflumizole, triforine, triticonazole, uniconazole, uniconazole-P, validamycin, valifenalate, vinclozolin, zarilamid, zinc naphthenate, zineb, ziram, or zoxamide.

Herbicides

Non-limiting examples of herbicides that may be used in combination the pyridine triazole compounds of formula I may include 2,3,6-TBA, 2,3,6-TBA-dimethylammonium, 2,3,6-TBA-sodium, 2,4,5-T, 2,4,5-T-2-butoxypropyl, 2,4,5-T-2-ethylhexyl, 2,4,5-T-3-butoxypropyl, 2,4,5-TB, 2,4,5-T-butometyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 3,4-DA, 3,4-DB, 3,4-DP, 4-CPA, 4-CPB, 4-CPP, acetochlor, acifluorfen, acifluorfen-methyl, acifluorfen-sodium, aclonifen, acrolein, alachlor, allidochlor, alloxydim, alloxydim-sodium, allyl alcohol, alorac, ametridione, ametryn, amibuzin, amicarbazone, amidosulfuron, amino cyclopyrachlor, amino cyclopyrachlor-methyl, amino cyclopyrachlor-potassium, aminopyralid, aminopyralid-potassium, aminopyralid-tris(2-hydroxypropyl)ammonium, amiprofos-methyl, amitrole, ammonium sulfamate, anilofos, anisuron, asulam, asulam-potassium, asulam-sodium, atraton, atrazine, azafenidin, azimsulfuron, aziprotryne, barban, BCPC, beflubutamid, benazolin, benazolin-dimethylammonium, benazolin-ethyl, benazolin-potassium, bencarbazone, benfluralin, benfuresate, bensulfuron, bensulfuron-methyl, bensulide, bentazone, bentazone-sodium, benzadox, benzadox-ammonium, benzfendizone, benzipram, benzobicyclon, benzofenap, benzofluor, benzoylprop, benzoylprop-ethyl, benzthiazuron, bicyclopyrone, bifenox, bilanafos, bilanafos-sodium, bispyribac, bispyribac-sodium, borax, bromacil, bromacil-lithium, bromacil-sodium, bromobonil, bromobutide, bromofenoxim, bromoxynil, bromoxynil butyrate, bromoxynil heptanoate, bromoxynil octanoate, bromoxynil-potassium, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, carfentrazone, carfentrazone-ethyl, CDEA, CEPC, chlomethoxyfen, chloramben, chloramben-ammonium, chloramben-diolamine, chloramben-methyl, chloramben-methylammonium, chloramben-sodium, chloranocryl, chlorazifop, chlorazifop-propargyl, chlorazine, chlorbromuron, chlorbufam, chloreturon, chlorfenac, chlorfenac-sodium, chlorfenprop, chlorfenprop-methyl, chlorflurazole, chlorflurenol, chlorflurenol-methyl, chloridazon, chlorimuron, chlorimuron-ethyl, chlornitrofen, chloropon, chlorotoluron, chloroxuron, chloroxynil, chlorprocarb, chlorpropham, chlorsulfuron, chlorthal, chlorthal-dimethyl, chlorthal-monomethyl, chlorthiamid, cinidon-ethyl, cinmethylin, cinosulfuron, cisanilide, clethodim, cliodinate, clodinafop, clodinafop-propargyl, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloransulam, cloransulam-methyl, CMA, copper sulfate, CPMF, CPPC, credazine, cresol, cumyluron, cyanamide, cyanatryn, cyanazine, cycloate, cyclosulfamuron, cycloxydim, cycluron, cyhalofop, cyhalofop-butyl, cyperquat, cyperquat chloride, cyprazine, cyprazole, cypromid, daimuron, dalapon, dalapon-calcium, dalapon-magnesium, dalapon-sodium, dazomet, dazomet-sodium, delachlor, desmedipham, desmetryn, di-allate, dicamba, dicamba-dimethylammonium, dicamba-diolamine, dicamba-isopropylammonium, dicamba-methyl, dicamba-olamine, dicamba-potassium, dicamba-sodium, dicamba-trolamine, dichlobenil, dichloralurea, dichlormate, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-dimethylammonium, dichlorprop-potassium, dichlorprop-sodium, diclofop, diclofop-methyl, diclosulam, diethamquat, diethamquat dichloride, diethatyl, diethatyl-ethyl, difenopenten, difenopenten-ethyl, difenoxuron, difenzoquat, difenzoquat metilsulfate, diflufenican, diflufenzopyr, diflufenzopyr-sodium, dimefuron, dimepiperate, dimethachlor, dimethametryn, dimethenamid, dimethenamid-P, dimexano, dimidazon, dinitramine, dinofenate, dinoprop, dinosam, dinoseb, dinoseb acetate, dinoseb-ammonium, dinoseb-diolamine, dinoseb-sodium, dinoseb-trolamine, dinoterb, dinoterb acetate, diphacinone-sodium, diphenamid, dipropetryn, diquat, diquat dibromide, disul, disul-sodium, dithiopyr, diuron, DMPA, DNOC, DNOC-ammonium, DNOC-potassium, DNOC-sodium, DSMA, EBEP, eglinazine, eglinazine-ethyl, endothal, endothal-diammonium, endothal-dipotassium, endothal-disodium, epronaz, EPTC, erbon, esprocarb, ethalfluralin, ethametsulfuron, ethametsulfuron-methyl, ethidimuron, ethiolate, ethofumesate, ethoxyfen, ethoxyfen-ethyl, ethoxysulfuron, etinofen, etnipromid, etobenzanid, EXD, fenasulam, fenoprop, fenoprop-3-butoxypropyl, fenoprop-butometyl, fenoprop-butotyl, fenoprop-butyl, fenoprop-isoctyl, fenoprop-methyl, fenoprop-potassium, fenoxaprop, fenoxaprop-ethyl, fenoxaprop-P, fenoxaprop-P-ethyl, fenoxasulfone, fenteracol, fenthiaprop, fenthiaprop-ethyl, fentrazamide, fenuron, fenuron TCA, ferrous sulfate, flamprop, flamprop-isopropyl, flamprop-M, flamprop-methyl, flamprop-M-isopropyl, flamprop-M-methyl, flazasulfuron, florasulam, fluazifop, fluazifop-butyl, fluazifop-methyl, fluazifop-P, fluazifop-P-butyl, fluazolate, flucarbazone, flucarbazone-sodium, flucetosulfuron, fluchloralin, flufenacet, flufenican, flufenpyr, flufenpyr-ethyl, flumetsulam, flumezin, flumiclorac, flumiclorac-pentyl, flumioxazin, flumipropyn, fluometuron, fluorodifen, fluoroglycofen, fluoroglycofen-ethyl, fluoromidine, fluoronitrofen, fluothiuron, flupoxam, flupropacil, flupropanate, flupropanate-sodium, flupyrsulfuron, flupyrsulfuron-methyl-sodium, fluridone, flurochloridone, fluroxypyr, fluroxypyr-butometyl, fluroxypyr-meptyl, flurtamone, fluthiacet, fluthiacet-methyl, fomesafen, fomesafen-sodium, foramsulfuron, fosamine, fosamine-ammonium, furyloxyfen, glufosinate, glufosinate-ammonium, glufosinate-P, glufosinate-P-ammonium, glufosinate-P-sodium, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, hexachloroacetone, hexaflurate, hexazinone, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, indanofan, indaziflam, iodobonil, iodomethane, iodosulfuron, iodosulfuron-methyl-sodium, ioxynil, ioxynil octanoate, ioxynil-lithium, ioxynil-sodium, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-dimethylammonium, mecoprop-P-isobutyl, mecoprop-potassium, mecoprop-P-potassium, mecoprop-sodium, mecoprop-trolamine, medinoterb, medinoterb acetate, mefenacet, mefluidide, mefluidide-diolamine, mefluidide-potassium, mesoprazine, mesosulfuron, mesosulfuron-methyl, mesotrione, metam, metam-ammonium, metamifop, metamitron, metam-potassium, metam-sodium, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metolachlor, metosulam, metoxuron, metribuzin, metsulfuron, metsulfuron-methyl, molinate, monalide, monisouron, monochloroacetic acid, monolinuron, monuron, monuron TCA, morfamquat, morfamquat dichloride, MSMA, naproanilide, napropamide, naptalam, naptalam-sodium, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxapyrazon-dimolamine, oxapyrazon-sodium, oxasulfuron, oxaziclomefone, oxyfluorfen, parafluron, paraquat, paraquat dichloride, paraquat dimetilsulfate, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picloram-2-ethylhexyl, picloram-isoctyl, picloram-methyl, picloramolamine, picloram-potassium, picloram-triethylammonium, picloram-tris(2-hydroxypropyl)ammonium, picolinafen, pinoxaden, piperophos, potassium arsenite, potassium azide, potassium cyanate, pretilachlor, primisulfuron, primisulfuron-methyl, procyazine, prodiamine, profluazol, profluralin, profoxydim, proglinazine, proglinazine-ethyl, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, proxan, proxan-sodium, prynachlor, pydanon, pyraclonil, pyraflufen, pyraflufen-ethyl, pyrasulfotole, pyrazolynate, pyrazosulfuron, pyrazosulfuron-ethyl, pyrazoxyfen, pyribenzoxim, pyributicarb, pyriclor, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quinonamid, quizalofop, quizalofop-ethyl, quizalofop-P, quizalofop-P-ethyl, quizalofop-P-tefuryl, rhodethanil, rimsulfuron, saflufenacil, sebuthylazine, secbumeton, sethoxydim, siduron, simazine, simeton, simetryn, SMA, S-metolachlor, sodium arsenite, sodium azide, sodium chlorate, sulcotrione, sulfallate, sulfentrazone, sulfometuron, sulfometuron-methyl, sulfosulfuron, sulfuric acid, sulglycapin, swep, TCA, TCA-ammonium, TCA-calcium, TCA-ethadyl, TCA-magnesium, TCA-sodium, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone, thiencarbazone-methyl, thifensulfuron, thifensulfuron-methyl, thiobencarb, tiocarbazil, tioclorim, topramezone, tralkoxydim, tri-allate, triasulfuron, triaziflam, tribenuron, tribenuron-methyl, tricamba, triclopyr, triclopyr-butotyl, triclopyr-ethyl, triclopyr-triethylammonium, tridiphane, trietazine, trifloxysulfuron, trifloxysulfuron-sodium, trifluralin, triflusulfuron, triflusulfuron-methyl, trifop, trifop-methyl, trifopsime, trihydroxytriazine, trimeturon, tripropindan, tritac, tritosulfuron, vernolate, or xylachlor.

Biopesticides

The pyridine triazole compounds of formula I may also be used in combination (such as in a compositional mixture, or a simultaneous or sequential application) with one or more biopesticides. The term "biopesticide" is used for microbial biological pest control agents that are applied in a similar manner to chemical pesticides. Commonly these are bacterial, but there are also examples of fungal control agents, including *Trichoderma* spp. and *Ampelomyces quisqualis* (a control agent for grape powdery mildew). *Bacillus subtilis* are used to control plant pathogens. Weeds and rodents have also been controlled with microbial agents. One well-known insecticide example is *Bacillus thuringiensis*, a bacterial disease of Lepidoptera, Coleoptera, and Diptera. Because it has little effect on other organisms, it is considered more environmentally friendly than synthetic pesticides. Biological insecticides include products based on:

1. entomopathogenic fungi (e.g. *Metarhizium anisopliae*);
2. entomopathogenic nematodes (e.g. *Steinernema feltiae*); and
3. entomopathogenic viruses (e.g. *Cydia pomonella* granulovirus).

Other examples of entomopathogenic organisms include, but are not limited to, baculoviruses, bacteria and other prokaryotic organisms, fungi, protozoa and Microsproridia. Biologically derived insecticides include, but not limited to, rotenone, veratridine, as well as microbial toxins; insect tolerant or resistant plant varieties; and organisms modified by recombinant DNA technology to either produce insecticides or to convey an insect resistant property to the genetically modified organism. In one embodiment, the molecules of Formula One may be used with one or more biopesticides in the area of seed treatments and soil amendments. *The Manual of Biocontrol Agents* gives a review of the available biological insecticide (and other biology-based control) products. Copping L. G. (ed.) (2004). *The Manual of Biocontrol Agents* (formerly the *Biopesticide Manual*) 3rd Edition. British Crop Production Council (BCPC), Farnham, Surrey UK.

Other Active Compounds

The pyridine triazole compounds of formula I may also be used in combination (such as in a compositional mixture, or a simultaneous or sequential application) with one or more of the following:

1. 3-(4-chloro-2,6-dimethylphenyl)-4-hydroxy-8-oxa-1-azaspiro[4,5]dec-3-en-2-one;
2. 3-(4'-chloro-2,4-dimethyl[1,1'-biphenyl]-3-yl)-4-hydroxy-8-oxa-1-azaspiro[4,5]dec-3-en-2-one;
3. 4-[[(6-chloro-3-pyridinyl)methyl]methylamino]-2(5H)-furanone;
4. 4-[[(6-chloro-3-pyridinyl)methyl]cyclopropylamino]-2(5H)-furanone;
5. 3-chloro-N2-[(1S)-1-methyl-2-(methylsulfonyl)ethyl]-N1-[2-methyl-4-[1,2,2,2-tetrafluoro-1-(trifluoromethyl)ethyl]phenyl]-1,2-benzenedicarboxamide;
6. 2-cyano-N-ethyl-4-fluoro-3-methoxy-benenesulfonamide;
7. 2-cyano-N-ethyl-3-methoxy-benzenesulfonamide;
8. 2-cyano-3-difluoromethoxy-N-ethyl-4-fluoro-benzenesulfonamide;
9. 2-cyano-3-fluoromethoxy-N-ethyl-benzenesulfonamide;
10. 2-cyano-6-fluoro-3-methoxy-N,N-dimethyl-benzenesulfonamide;
11. 2-cyano-N-ethyl-6-fluoro-3-methoxy-N-methyl-benzenesulfonamide;
12. 2-cyano-3-difluoromethoxy-N,N-dimethylbenzenesulfon-amide;
13. 3-(difluoromethyl)-N-[2-(3,3-dimethylbutyl)phenyl]-1-methyl-1H-pyrazole-4-carboxamide;
14. N-ethyl-2,2-dimethylpropionamide-2-(2,6-dichloro-α,α,α-trifluoro-p-tolyl) hydrazone;
15. N-ethyl-2,2-dichloro-1-methylcyclopropane-carboxamide-2-(2,6-dichloro-α,α,α-trifluoro-p-tolyl) hydrazone nicotine;
16. O-{(E-)-[2-(4-chloro-phenyl)-2-cyano-1-(2-trifluoromethylphenyl)-vinyl]}S-methyl thiocarbonate;
17. (E)-N1-[(2-chloro-1,3-thiazol-5-ylmethyl)]-N2-cyano-N1-methylacetamidine;
18. 1-(6-chloropyridin-3-ylmethyl)-7-methyl-8-nitro-1,2,3,5,6,7-hexahydro-imidazo[1,2-a]pyridin-5-ol;
19. 4-[4-chlorophenyl-(2-butylidine-hydrazono)methyl)] phenyl mesylate; and
20. N-ethyl-2,2-dichloro-1-methylcyclopropanecarboxamide-2-(2,6-dichloro-α,α,α-trifluoro-p-tolyl)hydrazone.

The pyridine triazole compounds of formula I may also be used in combination (such as in a compositional mixture, or a simultaneous or sequential application) with one or more compounds in the following groups: algicides, antifeedants, avicides, bactericides, bird repellents, chemosterilants, herbicide safeners, insect attractants, insect repellents, mammal repellents, mating disrupters, molluscicides, plant activators, plant growth regulators, rodenticides, or virucides.

Synergistic Mixtures and Synergists

The pyridine triazole compounds of formula I may be used in combination with at least one other insecticides to form a synergistic mixture where the mode of action of such compounds compared to the mode of action of the pyridine triazole compounds of formula I are the same, similar, or different. Examples of modes of action may include, but are not limited to: acetylcholinesterase inhibitor; sodium channel modulator; chitin biosynthesis inhibitor; GABA-gated chloride channel antagonist; GABA and glutamate-gated chloride channel agonist; acetylcholine receptor agonist; MET I inhibitor; Mg-stimulated ATPase inhibitor; nicotinic acetylcholine receptor; Midgut membrane disrupter; oxidative phosphorylation disrupter, or ryanodine receptor (RyRs).

Additionally, the pyridine triazole compounds of formula I may be used in combination with at least one of fungicides, acaricides, herbicides or nematicides to form a synergistic mixture.

Furthermore, the pyridine triazole compounds of formula I may be used in combination with other active compounds, such as the compounds under the heading "OTHER ACTIVE COMPOUNDS," algicides, avicides, bactericides, molluscicides, rodenticides, virucides, herbicide safeners, adjuvants, and/or surfactants to form a synergistic mixture. Moreover, the following compounds are known as synergists and may be used in combination with the pyridine triazole compounds of formula I: piperonyl butoxide, pipriotal, propyl isome, sesamex, sesamolin, sulfoxide, and tribufos.

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions. For further information on formulation types see "Catalogue of Pesticide Formulation Types and International Coding System" Technical Monograph n°2, 5th Edition by CropLife International (2002).

Pesticides are applied most often as aqueous suspensions or emulsions prepared from concentrated formulations of such pesticides. Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually selected from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are selected from conventional anionic and non-ionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They can be used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use, this embodiment will be referred to as "OIWE."

For further information consult "Insect Pest Management" 2nd Edition by D. Dent, copyright CAB International (2000). Additionally, for more detailed information consult "Handbook of Pest Control—The Behavior, Life History, and Control of Household Pests" by Arnold Mallis, 9th Edition, copyright 2004 by GIE Media Inc.

Other Formulation Components

Generally, when the pyridine triazole compounds of formula I or any agriculturally acceptable salt thereof, are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, antifoam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic "backbones" and a large number of ethylene oxide chains forming the "teeth" of a "comb" surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, oil-in-water emulsions, suspoemulsions, and ultra low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, bentonite, magnesium aluminum silicate, and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms can cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g. plant and animal sources. Specific examples are: vegetable oils, seed oils, and esters thereof, also alkoxylated alkyl polyglucosides.

For further information, see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

Pesticidal Activities

The disclosed pesticidal compositions may be used, for example, as nematicides, acaricides, pesticides, insecticides, miticides, and/or molluscicides.

In one particular embodiment, a method of controlling pests comprises applying a pesticidal composition comprising a pyridine triazole compounds of formula I or any agriculturally acceptable salt thereof near a population of pests.

The pyridine triazole compounds of formula I are generally used in amounts from about 0.01 grams per hectare to about 5000 grams per hectare to provide control. Amounts from about 0.1 grams per hectare to about 500 grams per hectare are generally preferred, and amounts from about 1 gram per hectare to about 50 grams per hectare are generally more preferred.

The area to which a pyridine triazole compounds of formula I is applied can be any area inhabited (or maybe inhabited, or traversed by) a pest, for example: where crops, trees, fruits, cereals, fodder species, vines, turf and ornamental plants, are growing; where domesticated animals are residing; the interior or exterior surfaces of buildings (such as places where grains are stored), the materials of construction used in building (such as impregnated wood), and the soil around buildings. Particular crop areas to use a molecule of Formula One include areas where apples, corn, sunflowers, cotton, soybeans, canola, wheat, rice, sorghum, barley, oats, potatoes, oranges, alfalfa, lettuce, strawberries, tomatoes, peppers, crucifers, pears, tobacco, almonds, sugar beets, beans and other valuable crops are growing or the seeds thereof are going to be planted. It is also advantageous to use ammonium sulfate with a 3-(thiazol-2-yl)pyridine 1-oxide compound when growing various plants.

Controlling pests generally means that pest populations, pest activity, or both, are reduced in an area. This can come about when: pest populations are repulsed from an area; when pests are incapacitated in or around an area; or pests are exterminated, in whole, or in part, in or around an area. Of course, a combination of these results can occur. Generally, pest populations, activity, or both are desirably reduced more than fifty percent, preferably more than 90 percent. Generally, the area is not in or on a human; consequently, the locus is generally a non-human area.

The pyridine triazole compounds of formula I may be used in mixtures, applied simultaneously or sequentially, alone or with other compounds to enhance plant vigor (e.g. to grow a better root system, to better withstand stressful growing conditions). Such other compounds are, for example, compounds that modulate plant ethylene receptors, most notably 1-methylcyclopropene (also known as 1-MCP). Furthermore, such molecules may be used during times when pest activity is low, such as before the plants that are growing begin to produce valuable agricultural commodities. Such times include the early planting season when pest pressure is usually low.

The pyridine triazole compounds of formula I can be applied to the foliar and fruiting portions of plants to control pests. The molecules will either come in direct contact with the pest, or the pest will consume the pesticide when eating leaf, fruit mass, or extracting sap, that contains the pesticide. The pyridine triazole compounds of formula I can also be applied to the soil, and when applied in this manner, root and stem feeding pests can be controlled. The roots can absorb a molecule taking it up into the foliar portions of the plant to control above ground chewing and sap feeding pests.

Generally, with baits, the baits are placed in the ground where, for example, termites can come into contact with, and/or be attracted to, the bait. Baits can also be applied to a surface of a building, (horizontal, vertical, or slant surface) where, for example, ants, termites, cockroaches, and flies, can come into contact with, and/or be attracted to, the bait. Baits can comprise a pyridine triazole compounds of formula I.

The pyridine triazole compounds of formula I can be encapsulated inside, or placed on the surface of a capsule. The size of the capsules can range from nanometer size (about 100-900 nanometers in diameter) to micrometer size (about 10-900 microns in diameter).

Because of the unique ability of the eggs of some pests to resist certain pesticides, repeated applications of the pyridine triazole compounds of formula I may be desirable to control newly emerged larvae.

Systemic movement of pesticides in plants may be utilized to control pests on one portion of the plant by applying (for example by spraying an area) the pyridine triazole compounds of formula I to a different portion of the plant. For example, control of foliar-feeding insects can be achieved by drip irrigation or furrow application, by treating the soil with for example pre- or post-planting soil drench, or by treating the seeds of a plant before planting.

Seed treatment can be applied to all types of seeds, including those from which plants genetically modified to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement, drought resistance, or any other beneficial traits. Furthermore, such seed treatments with the pyridine triazole compounds of formula I may further enhance the ability of a plant to better withstand stressful growing conditions. This results in a healthier, more vigorous plant, which can lead to higher yields at harvest time. Generally, about 1 gram of the pyridine triazole compounds of formula I to about 500 grams per 100,000 seeds is expected to provide good benefits, amounts from about 10 grams to about 100 grams per 100,000 seeds is expected to provide better benefits, and amounts from about 25 grams to about 75 grams per 100,000 seeds is expected to provide even better benefits.

It should be readily apparent that the pyridine triazole compounds of formula I may be used on, in, or around plants genetically modified to express specialized traits, such as *Bacillus thuringiensis* or other insecticidal toxins, or those expressing herbicide resistance, or those with "stacked"

foreign genes expressing insecticidal toxins, herbicide resistance, nutrition-enhancement, or any other beneficial traits.

The pyridine triazole compounds of formula I may be used for controlling endoparasites and ectoparasites in the veterinary medicine sector or in the field of non-human animal keeping. The pyridine triazole compounds of formula I are applied, such as by oral administration in the form of, for example, tablets, capsules, drinks, granules, by dermal application in the form of, for example, dipping, spraying, pouring on, spotting on, and dusting, and by parenteral administration in the form of, for example, an injection.

The pyridine triazole compounds of formula I may also be employed advantageously in livestock keeping, for example, cattle, sheep, pigs, chickens, and geese. They may also be employed advantageously in pets such as, horses, dogs, and cats. Particular pests to control would be fleas and ticks that are bothersome to such animals. Suitable formulations are administered orally to the animals with the drinking water or feed. The dosages and formulations that are suitable depend on the species.

The pyridine triazole compounds of formula I may also be used for controlling parasitic worms, especially of the intestine, in the animals listed above.

The pyridine triazole compounds of formula I may also be employed in therapeutic methods for human health care. Such methods include, but are limited to, oral administration in the form of, for example, tablets, capsules, drinks, granules, and by dermal application.

Pests around the world have been migrating to new environments (for such pest) and thereafter becoming a new invasive species in such new environment. The pyridine triazole compounds of formula I may also be used on such new invasive species to control them in such new environment.

The pyridine triazole compounds of formula I may also be used in an area where plants, such as crops, are growing (e.g. pre-planting, planting, pre-harvesting) and where there are low levels (even no actual presence) of pests that can commercially damage such plants. The use of such molecules in such area is to benefit the plants being grown in the area. Such benefits, may include, but are not limited to, improving the health of a plant, improving the yield of a plant (e.g. increased biomass and/or increased content of valuable ingredients), improving the vigor of a plant (e.g. improved plant growth and/or greener leaves), improving the quality of a plant (e.g. improved content or composition of certain ingredients), and improving the tolerance to abiotic and/or biotic stress of the plant.

Before a pesticide can be used or sold commercially, such pesticide undergoes lengthy evaluation processes by various governmental authorities (local, regional, state, national, and international). Voluminous data requirements are specified by regulatory authorities and must be addressed through data generation and submission by the product registrant or by a third party on the product registrant's behalf, often using a computer with a connection to the World Wide Web. These governmental authorities then review such data and if a determination of safety is concluded, provide the potential user or seller with product registration approval. Thereafter, in that locality where the product registration is granted and supported, such user or seller may use or sell such pesticide.

A pyridine triazole compounds of formula I can be tested to determine its efficacy against pests. Furthermore, mode of action studies can be conducted to determine if said molecule has a different mode of action than other pesticides. Thereafter, such acquired data can be disseminated, such as by the internet, to third parties.

The disclosed pesticidal composition comprising a pyridine triazole compounds of formula I may be used to control a wide variety of pests.

As a non-limiting example, in one or more embodiments, the method of the present disclosure may be used to control one or more members of *Lyriomiza sativae, Caliothrips phaseoli, Paratrioza cockerel, Spodoptera exigua, Myzus persicae, Nilaparvata lugens, Bemisia tabaci*, and *Myzus persicae*.

In additional embodiments, the method of the present disclosure may be used to control one or more members of at least one of Phylum Arthropoda, Phylum Nematoda, Subphylum Chelicerata, Subphylum Myriapoda, Subphylum Hexapoda, Class Insecta, Class Arachnida, and Class Symphyla. In at least some embodiments, the method of the present disclosure may be used to control one or more members of at least one of Class Insecta and Class Arachnida.

In further embodiments, the method of the present disclosure may be used to control members of the Order Coleoptera (beetles) including, but not limited to, *Acanthoscelides* spp. (weevils), *Acanthoscelides obtectus* (common bean weevil), *Agrilus planipennis* (emerald ash borer), *Agriotes* spp. (wireworms), *Anoplophora glabripennis* (Asian longhorned beetle), *Anthonomus* spp. (weevils), *Anthonomus grandis* (boll weevil), *Aphidius* spp., *Apion* spp. (weevils), *Apogonia* spp. (grubs), *Ataenius spretulus* (Black Turfgrass *Ataenius*), *Atomaria linearis* (pygmy mangold beetle), *Aulacophore* spp., *Bothynoderes punctiventris* (beet root weevil), *Bruchus* spp. (weevils), *Bruchus pisorum* (pea weevil), *Cacoesia* spp., *Callosobruchus maculatus* (southern cow pea weevil), *Carpophilus hemipteras* (dried fruit beetle), *Cassida vittata, Cerosterna* spp., *Cerotoma* spp. (chrysomelids), *Cerotoma trifurcata* (bean leaf beetle), *Ceutorhynchus* spp. (weevils), *Ceutorhynchus assimilis* (cabbage seedpod weevil), *Ceutorhynchus napi* (cabbage curculio), *Chaetocnema* spp. (chrysomelids), *Colaspis* spp. (soil beetles), *Conoderus scalaris, Conoderus stigmosus, Conotrachelus nenuphar* (plum curculio), *Cotinus nitidis* (Green June beetle), *Crioceris asparagi* (asparagus beetle), *Cryptolestes ferrugineus* (rusty grain beetle), *Cryptolestes pusillus* (flat grain beetle), *Cryptolestes turcicus* (Turkish grain beetle), *Ctenicera* spp. (wireworms), *Curculio* spp. (weevils), *Cyclocephala* spp. (grubs), *Cylindrocpturus adspersus* (sunflower stem weevil), *Deporaus marginatus* (mango leafcutting weevil), *Dermestes lardarius* (larder beetle), *Dermestes maculates* (hide beetle), *Diabrotica* spp. (chrysomelids), *Epilachna varivestis* (Mexican bean beetle), *Faustinus cubae, Hylobius* pales (pales weevil), *Hypera* spp. (weevils), *Hypera postica* (alfalfa weevil), *Hyperdoes* spp. (*Hyperodes weevil*), *Hypothenemus hampei* (coffee berry beetle), *Ips* spp. (engravers), *Lasioderma serricorne* (cigarette beetle), *Leptinotarsa decemlineata* (Colorado potato beetle), *Liogenys fuscus, Liogenys suturalis, Lissorhoptrus oryzophilus* (rice water weevil), *Lyctus* spp. (wood beetles/ powder post beetles), *Maecolaspis joliveti, Megascelis* spp., *Melanotus communis, Meligethes* spp., *Meligethes aeneus* (blossom beetle), *Melolontha melolontha* (common European cockchafer), *Oberea brevis, Oberea linearis, Oryctes rhinoceros* (date palm beetle), *Oryzaephilus mercator* (merchant grain beetle), *Oryzaephilus surinamensis* (sawtoothed grain beetle), *Otiorhynchus* spp. (weevils), *Oulema melanopus* (cereal leaf beetle), *Oulema oryzae, Pantomorus* spp. (weevils), *Phyllophaga* spp. (May/June beetle), *Phyllophaga cuyabana* (chrysomelids), *Phynchites* spp., *Popillia japonica* (Japanese beetle), *Prostephanus truncates* (larger grain borer), *Rhizopertha dominica* (lesser grain borer),

*Rhizotrogus* spp. (European chafer), *Rhynchophorus* spp. (weevils), *Scolytus* spp. (wood beetles), *Shenophorus* spp. (Billbug), *Sitona lineatus* (pea leaf weevil), *Sitophilus* spp. (grain weevils), *Sitophilus granaries* (granary weevil), *Sitophilus oryzae* (rice weevil), *Stegobium paniceum* (drugstore beetle), *Tribolium* spp. (flour beetles), *Tribolium castaneum* (red flour beetle), *Tribolium confusum* (confused flour beetle), *Trogoderma variabile* (warehouse beetle), and *Zabrus tenebioides*.

In other embodiments, the method of the present disclosure may also be used to control members of the Order Dermaptera (earwigs).

In additional embodiments, the method of the present disclosure may be used to control members of the Order Dictyoptera (cockroaches) including, but is not limited to, *Blattella germanica* (German cockroach), *Blatta orientalis* (oriental cockroach), *Parcoblatta pennylvanica*, *Periplaneta americana* (American cockroach), *Periplaneta australoasiae* (Australian cockroach), *Periplaneta brunnea* (brown cockroach), *Periplaneta fuliginosa* (smokybrown cockroach), *Pyncoselus suninamensis* (Surinam cockroach), and *Supella longipalpa* (brownbanded cockroach).

In further embodiments, the method of the present disclosure may be used to control members of the Order Diptera (true flies) including, but is not limited to, *Aedes* spp. (mosquitoes), *Agromyza frontella* (alfalfa blotch leafminer), *Agromyza* spp. (leaf miner flies), *Anastrepha* spp. (fruit flies), *Anastrepha suspensa* (Caribbean fruit fly), *Anopheles* spp. (mosquitoes), *Batrocera* spp. (fruit flies), *Bactrocera cucurbitae* (melon fly), *Bactrocera dorsalis* (oriental fruit fly), *Ceratitis* spp. (fruit flies), *Ceratitis capitata* (Mediterranean fruit fly), *Chrysops* spp. (deer flies), *Cochliomyia* spp. (screwworms), *Contarinia* spp. (Gall midges), *Culex* spp. (mosquitoes), *Dasineura* spp. (gall midges), *Dasineura brassicae* (cabbage gall midge), *Delia* spp., *Delia platura* (seedcorn maggot), *Drosophila* spp. (vinegar flies), *Fannia* spp. (filth flies), *Fannia canicularis* (little house fly), *Fannia scalaris* (latrine fly), *Gasterophilus intestinalis* (horse bot fly), *Gracillia perseae*, *Haematobia irritans* (horn fly), *Hylemyia* spp. (root maggots), *Hypoderma lineatum* (common cattle grub), *Liriomyza* spp. (leafminer flies), *Liriomyza brassica* (serpentine leafminer), *Melophagus ovinus* (sheep ked), *Musca* spp. (muscid flies), *Musca autumnalis* (face fly), *Musca domestica* (house fly), *Oestrus ovis* (sheep bot fly), *Oscinella frit* (frit fly), *Pegomyia betae* (beet leafminer), *Phorbia* spp., *Psila rosae* (carrot rust fly), *Rhagoletis cerasi* (cherry fruit fly), *Rhagoletis pomonella* (apple maggot), *Sitodiplosis mosellana* (orange wheat blossom midge), *Stomoxys calcitrans* (stable fly), *Tabanus* spp. (horse flies), and *Tipula* spp. (crane flies).

In other embodiments, the method of the present disclosure may be used to control members of the Order Hemiptera (true bugs) including, but is not limited to, *Acrosternum hilare* (green stink bug), *Blissus leucopterus* (chinch bug), *Calocoris norvegicus* (potato mirid), *Cimex hemipterus* (tropical bed bug), *Cimex lectularius* (bed bug), *Dagbertus fasciatus*, *Dichelops furcatus*, *Dysdercus suturellus* (cotton stainer), *Edessa meditabunda*, *Eurygaster maura* (cereal bug), *Euschistus heros*, *Euschistus servus* (brown stink bug), *Helopeltis antonii*, *Helopeltis theivora* (tea blight plantbug), *Lagynotomus* spp. (stink bugs), *Leptocorisa oratorius*, *Leptocorisa varicornis*, *Lygus* spp. (plant bugs), *Lygus hesperus* (western tarnished plant bug), *Maconellicoccus hirsutus*, *Neurocolpus longirostris*, *Nezara viridula* (southern green stink bug), *Phytocoris* spp. (plant bugs), *Phytocoris californicus*, *Phytocoris relativus*, *Piezodorus guildingi*, *Poecilocapsus lineatus* (fourlined plant bug), *Psallus vaccinicola*, *Pseudacysta perseae*, *Scaptocoris castanea*, and *Triatoma* spp. (bloodsucking conenose bugs/kissing bugs).

In additional embodiments, the method of the present disclosure may be used to control members of the Order Homoptera (aphids, scales, whiteflies, leaflhoppers) including, but is not limited to, *Acrythosiphon pisum* (pea aphid), *Adelges* spp. (adelgids), *Aleurodes proletella* (cabbage whitefly), *Aleurodicus disperses*, *Aleurothrixus floccosus* (woolly whitefly), *Aluacaspis* spp., *Amrasca bigutella bigutella*, *Aphrophora* spp. (leafhoppers), *Aonidiella aurantii* (California red scale), *Aphis* spp. (aphids), *Aphis gossypii* (cotton aphid), *Aphis pomi* (apple aphid), *Aulacorthum solani* (foxglove aphid), *Bemisia* spp. (whiteflies), *Bemisia argentifolii*, *Bemisia tabaci* (sweetpotato whitefly), *Brachycolus noxius* (Russian aphid), *Brachycorynella asparagi* (asparagus aphid), *Brevennia rehi*, *Brevicoryne brassicae* (cabbage aphid), *Ceroplastes* spp. (scales), *Ceroplastes rubens* (red wax scale), *Chionaspis* spp. (scales), *Chrysomphalus* spp. (scales), *Coccus* spp. (scales), *Dysaphis plantaginea* (rosy apple aphid), *Empoasca* spp. (leafhoppers), *Eriosoma lanigerum* (woolly apple aphid), *Icerya purchasi* (cottony cushion scale), *Idioscopus nitidulus* (mango leafhopper), *Laodelphax striatellus* (smaller brown planthopper), *Lepidosaphes* spp., *Macrosiphum* spp., *Macrosiphum euphorbiae* (potato aphid), *Macrosiphum granarium* (English grain aphid), *Macrosiphum rosae* (rose aphid), *Macrosteles quadrilineatus* (aster leafhopper), *Mahanarva frimbiolata*, *Metopolophium dirhodum* (rose grain aphid), *Mictis longicornis*, *Myzus* spp., *Myzus persicae* (green peach aphid), *Nephotettix* spp. (leafhoppers), *Nephotettix cinctipes* (green leafhopper), *Nilaparvata lugens* (brown planthopper), *Parlatoria pergandii* (chaff scale), *Parlatoria ziziphi* (ebony scale), *Peregrinus maidis* (corn delphacid), *Philaenus* spp. (spittlebugs), *Phylloxera vitifoliae* (grape phylloxera), *Physokermes piceae* (spruce bud scale), *Planococcus* spp. (mealybugs), *Pseudococcus* spp. (mealybugs), *Pseudococcus brevipes* (pine apple mealybug), *Quadraspidiotus perniciosus* (San Jose scale), *Rhapalosiphum* spp. (aphids), *Rhapalosiphum maida* (corn leaf aphid), *Rhapalosiphum padi* (oat bird-cherry aphid), *Saissetia* spp. (scales), *Saissetia oleae* (black scale), *Schizaphis graminum* (greenbug), *Sitobion avenae* (English grain aphid), *Sogatella furcifera* (white-backed planthopper), *Therioaphis* spp. (aphids), *Toumeyella* spp. (scales), *Toxoptera* spp. (aphids), *Trialeurodes* spp. (whiteflies), *Trialeurodes vaporariorum* (greenhouse whitefly), *Trialeurodes abutiloneus* (bandedwing whitefly), *Unaspis* spp. (scales), *Unaspis yanonensis* (arrowhead scale), and *Zulia entreriana*. In at least some embodiments, the method of the present disclosure may be used to control *Myzus persicae*.

In other embodiments, the method of the present disclosure may be used to control members of the Order Hymenoptera (ants, wasps, and bees) including, but not limited to, *Acromyrrmex* spp., *Athalia rosae*, *Atta* spp. (leafcutting ants), *Camponotus* spp. (carpenter ants), *Diprion* spp. (sawflies), *Formica* spp. (ants), *Iridomyrmex humilis* (Argentine ant), *Monomorium* ssp., *Monomorium minumum* (little black ant), *Monomorium pharaonis* (Pharaoh ant), *Neodiprion* spp. (sawflies), *Pogonomyrmex* spp. (harvester ants), *Polistes* spp. (paper wasps), *Solenopsis* spp. (fire ants), *Tapoinoma sessile* (odorous house ant), *Tetranomorium* spp. (pavement ants), *Vespula* spp. (yellow jackets), and *Xylocopa* spp. (carpenter bees).

In certain embodiments, the method of the present disclosure may be used to control members of the Order Isoptera (termites) including, but not limited to, *Coptotermes* spp., *Coptotermes curvignathus*, *Coptotermes*

*frenchii*, *Coptotermes formosanus* (Formosan subterranean termite), *Cornitermes* spp. (nasute termites), *Cryptotermes* spp. (drywood termites), *Heterotermes* spp. (desert subterranean termites), *Heterotermes aureus*, *Kalotermes* spp. (drywood termites), *Incistitermes* spp. (drywood termites), *Macrotermes* spp. (fungus growing termites), *Marginitermes* spp. (drywood termites), *Microcerotermes* spp. (harvester termites), *Microtermes obesi*, *Procornitermes* spp., *Reticulitermes* spp. (subterranean termites), *Reticulitermes banyulensis*, *Reticulitermes grassei*, *Reticulitermes flavipes* (eastern subterranean termite), *Reticulitermes hageni*, *Reticulitermes hesperus* (western subterranean termite), *Reticulitermes santonensis*, *Reticulitermes speratus*, *Reticulitermes tibialis*, *Reticulitermes virginicus*, *Schedorhinotermes* spp., and *Zootermopsis* spp. (rotten-wood termites).

In additional embodiments, the method of the present disclosure may be used to control members of the Order Lepidoptera (moths and butterflies) including, but not limited to, *Achoea janata*, *Adoxophyes* spp., *Adoxophyes orana*, *Agrotis* spp. (cutworms), *Agrotis ipsilon* (black cutworm), *Alabama argillacea* (cotton leafworm), *Amorbia cuneana*, *Amyelosis transitella* (navel orangeworm), *Anacamptodes defectaria*, *Anarsia lineatella* (peach twig borer), *Anomis sabulifera* (jute looper), *Anticarsia gemmatalis* (velvetbean caterpillar), *Archips argyrospila* (fruittree leafroller), *Archips rosana* (rose leaf roller), *Argyrotaenia* spp. (tortricid moths), *Argyrotaenia citrana* (orange tortrix), *Autographa gamma*, *Bonagota cranaodes*, *Borbo cinnara* (rice leaf folder), *Bucculatrix thurberiella* (cotton leafperforator), *Caloptilia* spp. (leaf miners), *Capua reticulana*, *Carposina niponensis* (peach fruit moth), *Chilo* spp., *Chlumetia transversa* (mango shoot borer), *Choristoneura rosaceana* (obliquebanded leafroller), *Chrysodeixis* spp., *Cnaphalocerus medinalis* (grass leafroller), *Colias* spp., *Conpomorpha cramerella*, *Cossus cossus* (carpenter moth), *Crambus* spp. (Sod webworms), *Cydiafunebrana* (plum fruit moth), *Cydia molesta* (oriental fruit moth), *Cydia nignicana* (pea moth), *Cydia pomonella* (codling moth), *Darna diducta*, *Diaphania* spp. (stem borers), *Diatraea* spp. (stalk borers), *Diatraea saccharalis* (sugarcane borer), *Diatraea graniosella* (southwester corn borer), *Earias* spp. (bollworms), *Earias insulata* (Egyptian bollworm), *Earias vitella* (rough northern bollworm), *Ecdytopopha aurantianum*, *Elasmopalpus lignosellus* (lesser cornstalk borer), *Epiphysias postruttana* (light brown apple moth), *Ephestia* spp. (flour moths), *Ephestia cautella* (almond moth), *Ephestia elutella* (tobbaco moth), *Ephestia kuehniella* (Mediterranean flour moth), *Epimeces* spp., *Epinotia aporema*, *Erionota thrax* (banana skipper), *Eupoecilia ambiguella* (grape berry moth), *Euxoa auxiliaris* (army cutworm), *Feltia* spp. (cutworms), *Gortyna* spp. (stemborers), *Grapholita molesta* (oriental fruit moth), *Hedylepta indicata* (bean leaf webber), *Helicoverpa* spp. (noctuid moths), *Helicoverpa armigera* (cotton bollworm), *Helicoverpa zea* (bollworm/corn earworm), *Heliothis* spp. (noctuid moths), *Heliothis virescens* (tobacco budworm), *Hellula undalis* (cabbage webworm), *Indarbela* spp. (root borers), *Keiferia lycopersicella* (tomato pinworm), *Leucinodes orbonalis* (eggplant fruit borer), *Leucoptera malifoliella*, *Lithocollectis* spp., *Lobesia botrana* (grape fruit moth), *Loxagrotis* spp. (noctuid moths), *Loxagrotis albicosta* (western bean cutworm), *Lymantria dispar* (gypsy moth), *Lyonetia clerkella* (apple leaf miner), *Mahasena corbetti* (oil palm bagworm), *Malacosoma* spp. (tent caterpillars), *Mamestra brassicae* (cabbage armyworm), *Maruca testulalis* (bean pod borer), *Metisa plana* (bagworm), *Mythimna unipuncta* (true armyworm), *Neoleucinodes elegantalis* (small tomato borer), *Nymphula depunctalis* (rice caseworm), *Operophthera brumata* (winter moth), *Ostrinia nubilalis* (European corn borer), *Oxydia vesulia*, *Pandemis cerasana* (common currant tortrix), *Pandemis heparana* (brown apple tortrix), *Papilio demodocus*, *Pectinophora gossypiella* (pink bollworm), *Peridroma* spp. (cutworms), *Peridroma saucia* (variegated cutworm), *Perileucoptera coffeella* (white coffee leafminer), *Phthorimaea operculella* (potato tuber moth), *Phyllocnisitis citrella*, *Phyllonorycter* spp. (leafminers), *Pieris rapae* (imported cabbageworm), *Plathypena scabs*, *Plodia interpunctella* (Indian meal moth), *Plutella xylostella* (diamondback moth), *Polychrosis viteana* (grape berry moth), *Prays endocarps*, *Prays oleae* (olive moth), *Pseudaletia* spp. (noctuid moths), *Pseudaletia unipunctata* (armyworm), *Pseudoplusia includens* (soybean looper), *Rachiplusia nu*, *Scirpophaga incertulas*, *Sesamia* spp. (stemborers), *Sesamia inferens* (pink rice stem borer), *Sesamia nonagrioides*, *Setora nitens*, *Sitotroga cerealella* (Angoumois grain moth), *Sparganothis pilleriana*, *Spodoptera* spp. (armyworms), *Spodoptera exigua* (beet armyworm), *Spodoptera fugiperda* (fall armyworm), *Spodoptera oridania* (southern armyworm), *Synanthedon* spp. (root borers), *Thecla basilides*, *Thermisia gemmatalis*, *Tineola bisselliella* (webbing clothes moth), *Trichoplusia ni* (cabbage looper), *Tuta absoluta*, *Yponomeuta* spp., *Zeuzera coffeae* (red branch borer), and *Zeuzera pyrina* (leopard moth). In at least some embodiments, the method of the present disclosure may be used to control *Spodoptera exigua*.

The method of the present disclosure may be used to also control members of the Order Mallophaga (chewing lice) including, but not limited to, *Bovicola ovis* (sheep biting louse), *Menacanthus stramineus* (chicken body louse), and *Menopon gallinea* (common hen louse).

In additional embodiments, the method of the present disclosure may be used to control members of the Order Orthoptera (grasshoppers, locusts, and crickets) including, but not limited to, *Anabrus simplex* (Mormon cricket), *Gryllotalpidae* (mole crickets), *Locusta migratoria*, *Melanoplus* spp. (grasshoppers), *Microcentrum retinerve* (angularwinged katydid), *Pterophylla* spp. (kaydids), *chistocerca gregaria*, *Scudderia furcata* (forktailed bush katydid), and *Valanga nigricorni*.

In other embodiments, the method of the present disclosure may be used to control members of the Order Phthiraptera (sucking lice) including, but not limited to, *Haematopinus* spp. (cattle and hog lice), *Linognathus ovillus* (sheep louse), *Pediculus humanus capitis* (human body louse), *Pediculus humanus humanus* (human body lice), and *Pthirus pubis* (crab louse).

In particular embodiments, the method of the present disclosure may be used to control members of the Order Siphonaptera (fleas) including, but not limited to, *Ctenocephalides canis* (dog flea), *Ctenocephalides felis* (cat flea), and *Pulex irritans* (human flea).

In additional embodiments, the method of the present disclosure may be used to control members of the Order Thysanoptera (thrips) including, but not limited to, *Frankliniella fusca* (tobacco thrips), *Frankliniella occidentalis* (western flower thrips), *Frankliniella shultzei*, *Frankliniella williamsi* (corn thrips), *Heliothrips haemorrhaidalis* (greenhouse thrips), *Riphiphorothrips cruentatus*, *Scirtothrips* spp., *Scirtothrips citri* (citrus thrips), *Scirtothrips dorsalis* (yellow tea thrips), *Taeniothrips rhopalantennalis*, and *Thrips* spp.

The method of the present disclosure may be used to also control members of the Order Thysanura (bristletails) including, but not limited to, *Lepisma* spp. (silverfish) and *Thermobia* spp. (firebrats).

In further embodiments, the method of the present disclosure may be used to control members of the Order Acari (mites and ticks) including, but not limited to, *Acarapsis woodi* (tracheal mite of honeybees), *Acarus* spp. (food mites), *Acarus siro* (grain mite), *Aceria mangiferae* (mango bud mite), *Aculops* spp., *Aculops lycopersici* (tomato russet mite), *Aculops pelekasi, Aculus pelekassi, Aculus schlechtendali* (apple rust mite), *Amblyomma americanum* (lone star tick), *Boophilus* spp. (ticks), *Brevipalpus obovatus* (privet mite), *Brevipalpus phoenicis* (red and black flat mite), *Demodex* spp. (mange mites), *Dermacentor* spp. (hard ticks), *Dermacentor variabilis* (american dog tick), *Dermatophagoides pteronyssinus* (house dust mite), *Eotetranycus* spp., *Eotetranychus carpini* (yellow spider mite), *Epitimerus* spp., *Eriophyes* spp., *Ixodes* spp. (ticks), *Metatetranycus* spp., *Notoedres cati, Oligonychus* spp., *Oligonychus coffee, Oligonychus ilicus* (southern red mite), *Panonychus* spp., *Panonychus citri* (citrus red mite), *Panonychus ulmi* (European red mite), *Phyllocoptruta oleivora* (citrus rust mite), *Polyphagotarsonemun latus* (broad mite), *Rhipicephalus sanguineus* (brown dog tick), *Rhizoglyphus* spp. (bulb mites), *Sarcoptes scabiei* (itch mite), *Tegolophus perseaflorae, Tetranychus* spp., *Tetranychus urticae* (twospotted spider mite), and *Varroa destructor* (honey bee mite).

In additional embodiments, the method of the present disclosure may be used to control members of the Order Nematoda (nematodes) including, but not limited to, *Aphelenchoides* spp. (foliar nematodes), *Belonolaimus* spp. (sting nematodes), *Criconemella* spp. (ring nematodes), *Dirofilaria immitis* (dog heartworm), *Ditylenchus* spp. (stem and bulb nematodes), *Heterodera* spp. (cyst nematodes), *Heterodera zeae* (corn cyst nematode), *Hirschmanniella* spp. (root nematodes), *Hoplolaimus* spp. (lance nematodes), *Meloidogyne* spp. (root knot nematodes), *Meloidogyne incognita* (root knot nematode), *Onchocerca volvulus* (hook-tail worm), *Pratylenchus* spp. (lesion nematodes), *Radopholus* spp. (burrowing nematodes), and *Rotylenchus reniformis* (kidney-shaped nematode).

In at least some embodiments, the method of the present disclosure may be used to control at least one insect in one or more of the Orders Lepidoptera, Coleoptera, Homoptera, Hemiptera, Thysanoptera, Isoptera, Orthoptera, Diptera, Hymenoptera, and Siphonaptera, and at least one mite in the Order Acari.

DETAILED DESCRIPTION

Insecticidal Testing

Example A

Bioassay for Green Peach Aphid (*Myzus persicae*) (GPA) (MYZUPE)

The green peach aphid (*Myzus persicae*) is the most significant aphid pest of peach trees, causing decreased growth, shriveling of the leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. GPA attacks such plants as broccoli, burdock, cabbage, carrot, cauliflower, daikon, eggplant, green beans, lettuce, macadamia, papaya, peppers, sweet potatoes, tomatoes, watercress, and zucchini, among other plants. GPA also attacks many ornamental crops such as carnation, chrysanthemum, flowering white cabbage, poinsettia, and roses. GPA has developed resistance to many pesticides.

Cabbage seedlings grown in 3-inch pots, with 2-3 small (3-5 cm) true leaves, were used as test substrate. The seedlings were infested with 20-50 GPA (wingless adult and nymph stages) one day prior to chemical application. Four pots with individual seedlings were used for each treatment. Test compounds (2 mg) were dissolved in 2 mL of acetone/methanol (1:1) solvent, forming stock solutions of 1000 ppm test compound. The stock solutions were diluted 5× with 0.025% Tween 20 in H2O to obtain the solution at 200 ppm test compound. A hand-held aspirator-type sprayer was used for spraying a solution to both sides of cabbage leaves until runoff Reference plants (solvent check) were sprayed with the diluent only containing 20% by volume of acetone/methanol (1:1) solvent. Treated plants were held in a holding room for three days at approximately 25° C. and ambient relative humidity (RH) prior to grading. Evaluation was conducted by counting the number of live aphids per plant under a microscope. Percent control was measured by using Abbott's correction formula (W. S. Abbott, "A Method of Computing the Effectiveness of an Insecticide," J. Econ. Entomol. 18 (1925), pp. 265-267) as follows Corrected % Control=100*(X−Y)/X where
X=No. of live aphids on solvent check plants and
Y=No. of live aphids on treated plants.

The results are indicated in the table entitled "TABLE 2. Biological Data for Green Peach Aphid (GPA) (MYZUPE) and Sweetpotato Whitefly-crawler (WF) (BEMITA)" (see Table section).

Example B

Insecticidal Test for Sweetpotato Whitefly-Crawler (WF) (*Bemisia tabaci*) (BEMITA) in Foliar Spray Assay The sweetpotato whitefly (*Bemisia tabaci*) has been reported as a serious pest of cultivated crops world-wide. It has an extremely wide host range attacking more than 500 species of plants from 63 plant families. Weeds often serve as alternate hosts of crop pests. Direct feeding damage is caused by the piercing and sucking sap from the foliage of plants. This feeding causes weakening and early wilting of the plant and reduces the plant growth rate and yield. Indirect damage results by the accumulation of honeydew produced by the whiteflies. Honeydew serves as a substrate for the growth of black sooty mold on leaves and fruit reducing photosynthesis and lessens the market value of the plant or yield. Damage is also caused when sweetpotato whitefly vectors plant viruses. The sweetpotato whitefly is considered the most common and important whitefly vector of plant viruses worldwide.

Cotton plants (*Gossypium hirsutum*) grown in 3-inch pots, with 1 small (4-5 cm) true leaves, were used as test substrate. The plants were infested with 200-400 whitefly eggs 4-5 days prior to chemical application. Four pots with individual plants were used for each treatment. Test compounds (2 mg) were dissolved in 1 mL of acetone solvent, forming stock solutions of 2000 ppm test compound. The stock solutions were diluted 10× with 0.025% Tween 20 in H2O (diluents)

to obtain the solution at 200 ppm test compound. A handheld aspirator-type sprayer was used for spraying a solution to both sides of cotton leaves until runoff. Reference plants (solvent check) were sprayed with the diluent only containing 10% by volume of acetone solvent. Treated plants were held in a holding room for 9 days at approximately 25° C. and ambient relative humidity (RH) prior to grading. Evaluation was conducted by counting the number of live 3-4 nymph stage per plant under a microscope. Percent control was measured by using Abbott's correction formula (W. S. Abbott, "A Method of Computing the Effectiveness of an Insecticide," J. Econ. Entomol. 18 (1925), pp. 265-267) as follows.

Corrected % Control=100*(X−Y)/X where

X=No. of live nymphs on solvent check plants and
Y=No. of live nymphs on treated plants.

The results are indicated in the table entitled "Table 2. Biological Data for Green Peach Aphid (MYZUPE) and Sweetpotato Whitefly-crawler (WF) (BEMITA)" (see Table section).

Insecticidal Testing

TABLE 2 shows the pesticidal activities of the disclosed pesticidal compounds against green peach aphid (GPA) and sweetpotato whitefly-crawler (WF). The mortality efficiency of the pesticidal compounds against GPA and WF insects was determined after treatment. The mortality efficiency of the disclosed pesticidal compounds against GPA and WF insects was rated as shown in TABLE 1.

TABLE 1

| Mortality Rating for Green Peach Aphid and Whitefly | |
|---|---|
| % Control (or Mortality) | Rating |
| 80-100 | A |
| More than 0-Less than 80 | B |
| Not Tested | C |
| No activity noticed in this bioassay | D |

TABLE 2

| Biological Data for Green Peach Aphid (MYZUPE) and Sweetpotato Whitefly-crawler (BEMITA) | | |
|---|---|---|
| | Insect species | |
| No. | GPA 200 ppm | WF 200 ppm |
| F1 | B | B |
| F2 | A | B |
| F3 | A | D |
| F4 | A | A |
| F5 | A | B |
| F6 | A | B |
| F7 | A | A |
| F8 | A | A |
| F9 | A | B |
| F10 | A | B |
| F11 | B | D |
| F12 | A | A |
| F13 | A | D |

The following examples serve to explain embodiments of the present invention in more detail. These examples should not be construed as being exhaustive or exclusive as to the scope of this invention.

EXAMPLES

These examples are for illustration purposes and are not to be construed as limiting the disclosure to only the embodiments disclosed in these examples.

Starting materials, reagents, and solvents that were obtained from commercial sources were used without further purification. Anhydrous solvents were purchased as SURE/SEAL™ from Aldrich and were used as received. Melting points were obtained using a Thomas Hoover Unimelt capillary melting point apparatus or an OptiMelt Automated Melting Point System from Stanford Research Systems and are uncorrected. Examples using "room temperature" were conducted in climate controlled laboratories with a temperature ranging from about 20° C. to about 24° C. Chemical compounds were given their known names, named according to naming programs within ISIS Draw, ChemDraw or ACD Name Pro. If such programs were unable to name the chemical compound, the chemical compound was named using conventional naming rules. $^1H$ NMR spectral data were in ppm (δ) and were recorded at 300, 400 or 600 MHz. $^{13}C$ NMR spectral data were in ppm (δ) and were recorded at 75, 100 or 150 MHz. $^{19}F$ NMR spectral data were in ppm (δ) and were recorded at 376 MHz, unless otherwise stated.

Example 1

Preparation of 2-[1-(pyridin-3-yl)-1H-1,2,3-triazol-4-yl]-6-(trifluoromethyl) pyridine Compound F7

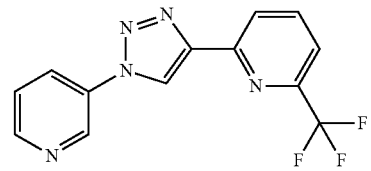 [SMILES: FC(F)(F)c1cccc(-c2cn(-c3cccnc3)nn2)n1]

A stirred solution of 3-(4-(tributylstannyl)-1H-1,2,3-triazol-1-yl)pyridine (0.396 g, 0.910 mmol) (prepared according to Bioorganic & Medicinal Chemistry 2008, 9817) in 1,4-dioxane (8.00 mL) was charged with 2-bromo-6-(trifluoromethyl)pyridine (0.248 g, 1.10 mmol), CuI (0.0510 g, 0.270 mmol), and Pd(PPh$_3$)$_2$Cl$_2$ (0.0630 g, 0.0900 mmol) sequentially at room temperature (about 22° C.) under a nitrogen atmosphere. The reaction mixture was evacuated and backfilled with nitrogen gas two or three times, and was heated to reflux (about 100° C.) for 4 hours. The reaction mixture was cooled and diluted with ethyl acetate (EtOAc, 20 mL), shaken well with 5% aqueous potassium fluoride (KF) solution (3×50 mL), and passed through a CELITE® bed. The organic layer was washed with brine solution (2×25 mL), dried over anhydrous sodium sulfate (Na$_2$SO$_4$), and concentrated under reduced pressure. The crude residue was purified by flash column chromatography (0-50% EtOAc/hexanes with 1% triethylamine as coeluent) to afford the title compound F7 as a solid (0.085 g, 32% yield).

The following compounds were prepared according to the procedures describes in Example 1:

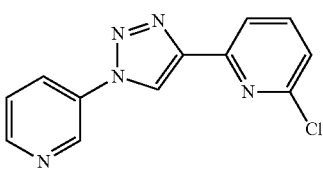 [SMILES: Clc1cccc(-c2cn(-c3cccnc3)nn2)n1]

2-Chloro-6-[1-(pyridin-3-yl)-1H-1,2,3-triazol-4-yl]pyridine (F10) was isolated in 34% yield.

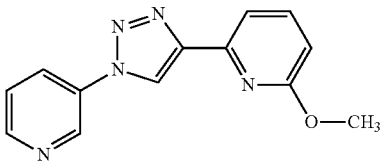 [SMILES: COc1cccc(-c2cn(-c3cccnc3)nn2)n1]

2-Methoxy-6-[1-(pyridin-3-yl)-1H-1,2,3-triazol-4-yl]pyridine (F5) was isolated in 40% yield.

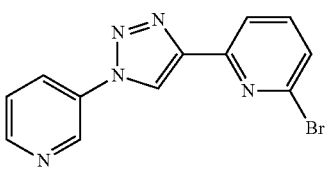 [SMILES: Brc1cccc(-c2cn(-c3cccnc3)nn2)n1]

2-Bromo-6-[1-(pyridin-3-yl)-1H-1,2,3-triazol-4-yl]pyridine (F9) was isolated in 32% yield.

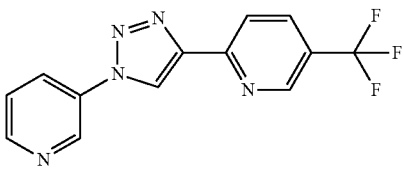 [SMILES: FC(F)(F)c1ccc(-c2cn(-c3cccnc3)nn2)nc1]

2-[1-(Pyridin-3-yl)-1H-1,2,3-triazol-4-yl]-5-(trifluoromethyl)pyridine (F8) was isolated in 36% yield.

Example 2

Preparation of 2-methyl-6-(1-(pyridin-3-yl)-1H-1,2,3-triazol-4-yl)pyridine Compound F12

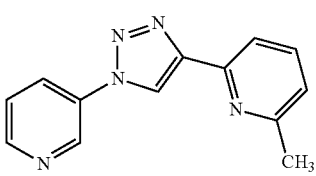 [SMILES: Cc1cccc(-c2cn(-c3cccnc3)nn2)n1]

A stirred solution of 3-(4-(tributylstannyl)-1H-1,2,3-triazol-1-yl)pyridine (0.348 g, 0.800 mmol) in 1,4-dioxane (10 mL) was charged with 2-bromo-6-methylpyridine (0.165 g, 0.960 mmol), CsF (0.243 g, 1.60 mmol), 4 Å molecular sieves (0.100 g), and [1,3-bis(2,6-diisopropylphenyl)-imidazol-2-ylidene]-(3-chloropyridyl)palladium(II) dichloride (Pd-PEPPSI-IPr) precatalyst (0.0200 g, 0.0300 mmol) successively at room temperature under a nitrogen atmosphere. The reaction mixture was evacuated and backfilled with nitrogen gas two or three times, and was heated at reflux for 4 hours. The reaction mixture was cooled to room temperature, diluted with EtOAc (20 mL), shaken well with 5% aqueous KF solution (3×50 mL), and passed through a CELITE® bed. The organic layer was washed with brine solution (2×25 mL), dried over anhydrous $Na_2SO_4$, and concentrated under reduced pressure. The crude residue was purified by flash column chromatography (0-100% EtOAc/hexanes with 1% triethylamine as coeluent) to afford the compound (F12) as a solid (0.0820 g, 44%).

The following compound was prepared according to the procedures disclosed in Example 2:

5-Methyl-2-[1-(pyridin-3-yl)-1H-1,2,3-triazol-4-yl]pyridine (F4), isolated in 40% yield.

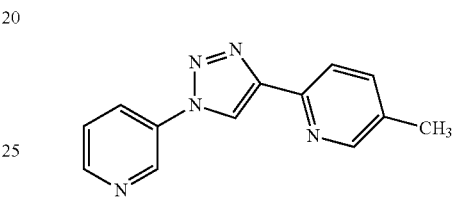

Example 3

Preparation of 3-(4-(3-(trifluoromethoxy)phenyl)-1H-1,2,3-triazol-1-yl)pyridine Compound F6

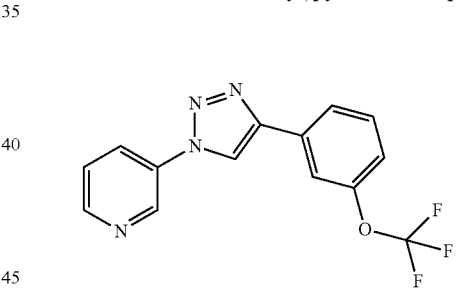

A stirred solution of 3-(4-iodo-1H-1,2,3-triazol-1-yl)pyridine (0.15 g, 0.55 mmol) in 1,4-dioxane (6.0 mL) and water (6.0 mL) was charged with (3-(trifluoromethoxy)phenyl)boronic acid (0.12 g, 0.60 mmol), $Na_2CO_3$ (29 mg, 0.27 mmol), and $Pd(PPh_3)_2Cl_2$ (21 mg, 0.03 mmol) sequentially at room temperature under a nitrogen atmosphere. The reaction flask was evacuated and backfilled with nitrogen gas two or three times, and was heated at reflux for 4 hours. The reaction mixture was diluted with water (20 mL) and extracted with EtOAc (2×50 mL). The combined organic layer was washed with brine solution (2×25 mL), dried over anhydrous $Na_2SO_4$, and concentrated under reduced pressure. The crude residue was purified by flash column chromatography (0-100% EtOAc/hexanes with 1% triethylamine as coeluent) to afford the title compound (F6) as a solid (0.12 g, 65%).

The following compounds were prepared according to the procedures disclosed in Example 3:

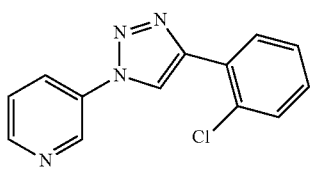 [SMILES: Clc1ccccc1-c1cn(-c2cccnc2)nn1]

3-[4-(2-Chlorophenyl)-1H-1,2,3-triazol-4-yl]pyridine (F1) was isolated in 53% yield.

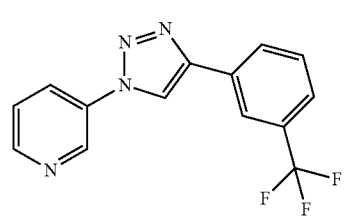 [SMILES: FC(F)(F)c1cccc(-c2cn(-c3cccnc3)nn2)c1]

3-{4-[3-(Trifluoromethyl)phenyl]-1H-1,2,3-triazol-4-yl}pyridine (F13) was isolated in 71% yield.

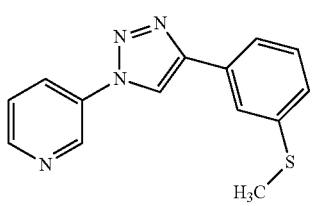 [SMILES: CSc1cccc(-c2cn(-c3cccnc3)nn2)c1]

3-{4-[3-(methylthio)phenyl]-1H-1,2,3-triazol-4-yl}pyridine (F3) was isolated in 44% yield.

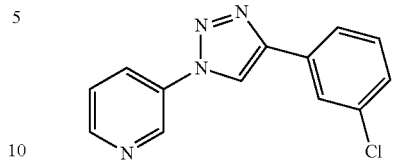

3-[4-(3-Chlorophenyl)-1H-1,2,3-triazol-4-yl]pyridine (F11) was isolated in 56% yield.

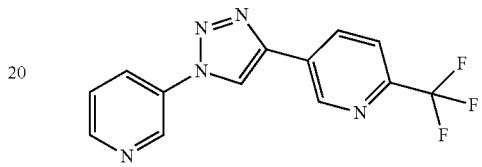

5-[1-(Pyridin-3-yl)-1H-1,2,3-triazol-4-yl]-2-(trifluoromethyl)pyridine (F2) was isolated in 71% yield.

TABLE 3 shows non-limiting examples of the pyridine triazole compounds of formula I. Compounds F1, F2, F3, F11, and F13 were prepared according to Example 3. Compounds F4, F6, and F12 were prepared according to Example 2. Compounds F5, F7, F8, F9, and F10 were prepared according to Example 1.

| No. | Structure | | ESIMS (m/z) | $^1$H NMR |
|---|---|---|---|---|
| F1 | 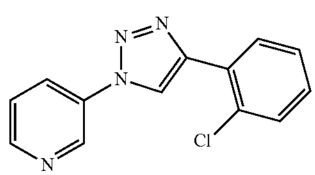 [SMILES: Clc1ccccc1-c1cn(-c2cccnc2)nn1] | Off-White Solid | 257.0 ([M + H]$^+$) | (400 MHz, CDCl$_3$) δ 9.11 (s, 1H), 8.76 (d, J = 4.0 Hz, 1H), 8.69 (s, 1H), 8.34 (dd, J = 8.0, 1.6 Hz, 1H), 8.24-8.21 (m, 1H), 7.57-7.51 (m, 2H), 7.44 (t, J = 7.6 Hz, 1H), 7.35 (t, J = 8.0 Hz, 1H) |
| F2 | 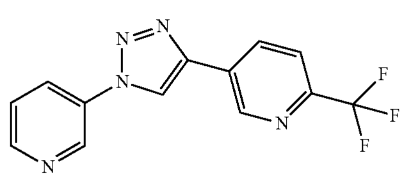 [SMILES: FC(F)(F)c1ccc(-c2cn(-c3cccnc3)nn2)cn1] | Off-White Solid | 292 ([M + H]$^+$) | $^1$H NMR (300 MHz, CDCl$_3$) δ 9.20 (d, J = 2.4 Hz, 1H), 9.10 (d, J = 2.4 Hz, 1H), 8.78 (dd, J = 4.8, 1.2 Hz, 1H), 8.50 (dd, J = 8.1, 1.2 Hz, 1H), 8.43 (s, 1H), 8.24-8.20 (m, 1H), 7.83 (d, J = 8.1 Hz, 1H), 7.59-7.55 (m, 1H) |
| F3 | 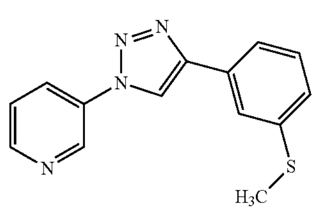 [SMILES: CSc1cccc(-c2cn(-c3cccnc3)nn2)c1] | Light Brown Solid | 269.0 ([M + H]$^+$) | $^1$H NMR (300 MHz, CDCl$_3$) δ 9.07 (d, J = 2.4 Hz, 1H), 8.73 (d, J = 4.0 Hz, 1H), 8.25 (s, 1H), 8.23-8.19 (m, 1H), 7.84 (s, 1H), 7.65 (d, J = 7.5 Hz, 1H), 7.56-7.51 (m, 1H), 7.39 (t, J = 7.5 Hz, 1H), 7.29 (s, 1H), 2.56 (s, 3H) |

-continued

| No. | Structure | | ESIMS (m/z) | ¹H NMR |
|---|---|---|---|---|
| F4 | 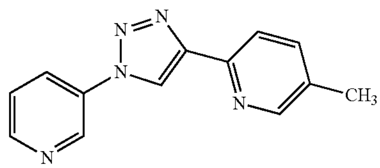 [SMILES: Cc1ccc(-c2cn(-c3cccnc3)nn2)nc1] | Off-White Solid | 238.1 ([M + H]⁺) | ¹H NMR (400 MHz, CDCl₃) δ 9.12 (d, J = 2.4 Hz, 1H), 8.73 (dd, J = 4.8, 1.6 Hz, 1H), 8.61 (s, 1H), 8.46 (s, 1H), 8.22-8.19 (m, 1H), 8.15 (d, J = 8.0 Hz, 1H), 7.64 (dd, J = 8.0, 1.2 Hz, 1H), 7.54-7.51 (m, 1H), 2.40 (s, 3H) |
| F5 | 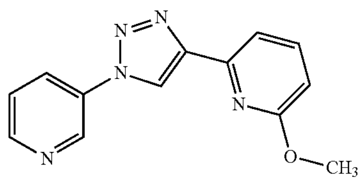 [SMILES: COc1cccc(-c2cn(-c3cccnc3)nn2)n1] | Light Yellow Solid | ESIMS m/z 254.1 ([M + H]⁺) | ¹H NMR (400 MHz, CDCl₃) δ 9.13 (d, J = 2.4 Hz, 1H), 8.76 (d, J = 4.0 Hz, 1H), 8.58 (s, 1H), 8.25 (d, J = 8.4 Hz, 1H), 7.86 (d, J = 7.6 Hz, 1H), 7.73 (t, J = 7.6 Hz, 1H), 7.57-7.54 (m, 1H), 6.77 (d, J = 8.4 Hz, 1H), 4.03 (s, 3H) |
| F6 | 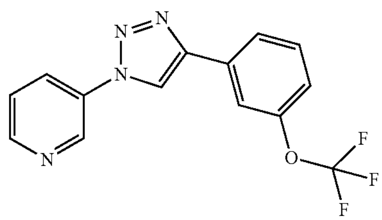 [SMILES: FC(F)(F)Oc1cccc(-c2cn(-c3cccnc3)nn2)c1] | Light Yellow Solid | ESIMS m/z 307 ([M + H]⁺) | ¹H NMR (400 MHz, CDCl₃) δ 9.08 (d, J = 2.4 Hz, 1H), 8.76 (d, J = 4.8 Hz, 1H), 8.29 (s, 1H), 8.23-8.20 (m, 1H), 7.86 (d, J = 8.0 Hz, 1H), 7.80 (s, 1H), 7.57-7.50 (m, 2H), 7.25 (s, 1H) |
| F7 | 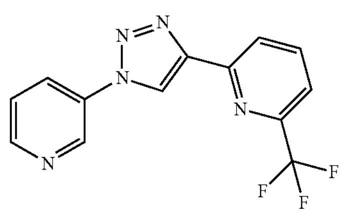 | Light Yellow Solid | ESIMS m/z 292.1 ([M + H]⁺) | ¹H NMR (400 MHz, CDCl₃) δ 9.15 (d, J = 2.4 Hz, 1H), 8.77-8.76 (m, 1H), 8.75 (s, 1H), 8.45 (d, J = 8.0 Hz, 1H), 8.23-8.20 (m, 1H), 8.02 (t, J = 8.0 Hz, 1H), 7.67 (d, J = 8.0 Hz, 1H), 7.57-7.53 (m, 1H) |
| F8 | 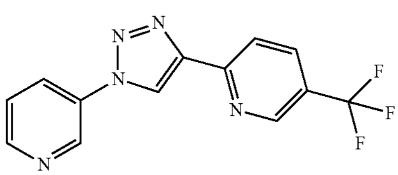 [SMILES: FC(F)(F)c1ccc(-c2cn(-c3cccnc3)nn2)nc1] | Off-White Solid | ESIMS m/z 292.0 ([M + H]⁺) | ¹H NMR (400 MHz, CDCl₃) δ 9.12 (d, J = 2.4 Hz, 1H), 8.88 (s, 1H), 8.76 (d, J = 4.0 Hz, 1H), 8.72 (s, 1H), 8.40 (d, J = 8.0 Hz, 1H), 8.24-8.21 (m, 1H), 8.08 (dd, J = 8.4, 2.0 Hz, 1H), 7.58-7.54 (m, 1H) |
| F9 | 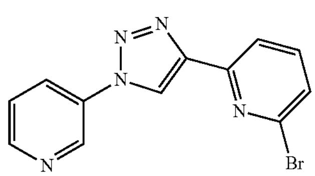 | Off-White Solid | 302/304 ([M + H]⁺) | ¹H NMR (400 MHz, CDCl₃) δ 9.11 (d, J = 2.4 Hz, 1H), 8.75 (dd, J = 4.8 Hz, 1.2 Hz, 1H), 8.69 (s, 1H), 8.23-8.18 (m, 2H), 7.68 (t, d, J = 8.0 Hz, 1H), 7.55-7.51 (m, 1H), 7.48-7.46 (m, 1H) |
| F10 | 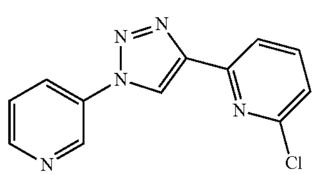 [SMILES: Clc1cccc(-c2cn(-c3cccnc3)nn2)n1] | Off-White Solid | 258.0 ([M + H]⁺) | ¹H NMR (400 MHz, CDCl₃) δ 9.11 (d, J = 2.4 Hz, 1H), 8.75 (dd, J = 4.8 Hz, 1.2 Hz, 1H), 8.69 (s, 1H), 8.21-8.18 (m, 2H), 7.80 (t, d, J = 8.0 Hz, 1H), 7.55-7.52 (m, 1H), 7.33 (d, J = 8.0 Hz, 1H) |
| F11 | 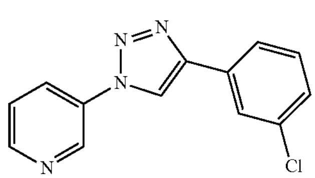 [SMILES: Clc1cccc(-c2cn(-c3cccnc3)nn2)c1] | Off-White Solid | 257.11 ([M + H]⁺) | ¹H NMR (400 MHz, CDCl₃) δ 9.07 (s, 1H), 8.76 (d, J = 4.0 Hz, 1H), 8.27 (s, 1H), 8.23-8.20 (m, 1H), 7.94 (s, 1H), 7.83 (d, J = 7.2 Hz, 1H), 7.57-7.54 (m, 1H), 7.45-7.36 (m, 2H) |

| No. | Structure | ESIMS (m/z) | ¹H NMR |
|---|---|---|---|
| F12 | Off-White Solid | 238.1 ([M + H]⁺) | ¹H NMR (300 MHz, CDCl₃) δ 9.12 (d, J = 2.4 Hz, 1H), 8.73 (dd, J = 4.8, 1.2 Hz, 1H), 8.66 (s, 1H), 8.24-8.21 (m, 1H), 8.05 (d, J = 11.4 Hz, 1H), 7.71 (t, d, J = 7.8 Hz, 1H), 7.55-7.51 (m, 1H), 7.15 (d, J = 7.8 Hz, 1H), 2.60 (s, 3H) |
| F13 | Off-White Solid | 291.0 ([M + H]⁺) | ¹H NMR (400 MHz, CDCl₃) δ 9.10 (s, 1H), 8.77 (s, 1H), 8.34 (s, 1H), 8.24-8.22 (m, 1H), 8.18 (s, 1H), 8.15 (d, J = 7.6 Hz, 1H), 7.68-7.55 (m, 3H) |

Example 4

Preparation of 2-(6-(1-(pyridin-3-yl)-1H-1,2,3-triazol-4-yl)pyridin-2-yl)pyrimidine Compound P1

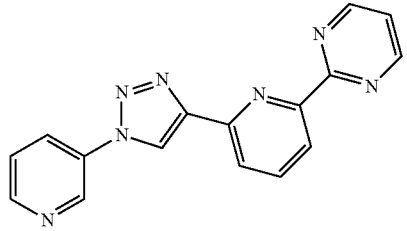 [SMILES: c1cnc(-c2cccc(-c3cn(-c4cccnc4)nn3)n2)nc1]

To (1-(pyridin-3-yl)-1H-1,2,3-triazol-4-yl)boronic acid in an appropriate reaction vessel may be added 2-(6-bromopyridin-2-yl)pyrimidine (from about 1 eq to about 1.5 eq) in a solvent, such as 1,4-dioxane at a concentration between about 0.01 M to about 1 M. Then, a base such as Na₂CO₃ (from about 1 eq to about 5 eq) and a catalyst such as Pd(PPh₃)₄ (from about 0.01 eq to about 0.5 eq) may be added. The reaction may be stirred at a temperature of from about 50° C. to about 150° C. until the reaction was determined to be completed. Following completion of the reaction, the product may be obtained using standard organic chemistry techniques of workup and purification.

The following compounds may be prepared according to the procedures disclosed in Example 4: P1, P2, and P3.

P1
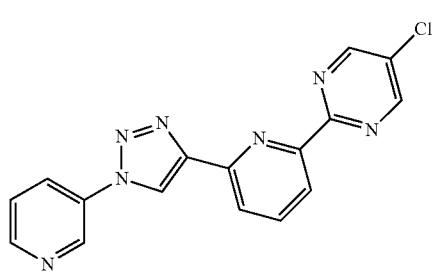

P2
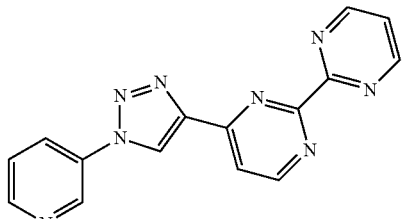

P3
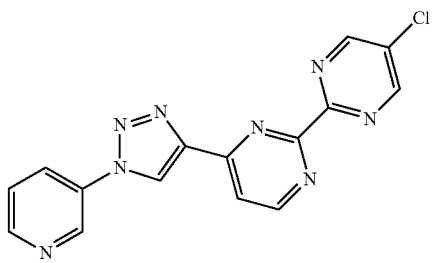

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

We claim:

1. A pesticidal composition, comprising a pyridine triazole compound of formula I, or any agriculturally acceptable salt thereof:

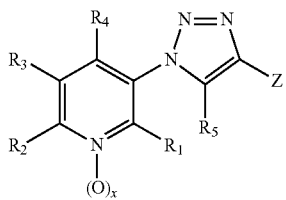

I wherein:
(a) $R_1$, $R_2$, and $R_4$ are independently hydrogen, F, Cl, Br, I, substituted or unsubstituted $C_1$-$C_6$ alkyl, or substituted or unsubstituted $C_1$-$C_6$ haloalkyl,
wherein each $R_1$, $R_2$, and $R_4$, when substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_3$-$C_{10}$ cycloalkyl, or $C_3$-$C_{10}$ halocycloalkyl, where each of which is unsubstituted or substituted with $R_{11}$;
(b) $R_3$ is hydrogen, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_3$-$C_{10}$ cycloalkyl, substituted or unsubstituted $C_1$-$C_6$ haloalkyl, substituted or unsubstituted $C_6$-$C_{20}$ aryl, substituted or unsubstituted $C_1$-$C_{20}$ heterocyclyl, $OR_{11}$, $C(=X_1)R_{11}$, $C(=X_1)R_{11}$, $C(=X_1)N(R_{11})_2$, $N(R_{11})_2$, $N(R_{11})C(=X_1)R_{11}$, $SR_{11}$, $S(O)_nOR_{11}$, or $R_{11}S(O)_nR_{11}$,
wherein $R_3$, when substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, $OR_{11}$, $S(O)_nOR_{11}$, $C_6$-$C_{20}$ aryl, or $C_1$-$C_{20}$ heterocyclyl, wherein each of which is unsubstituted or substituted with $R_{11}$;
(c) $R_5$ is hydrogen, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, $C_3$-$C_{10}$ cycloalkyl, substituted or unsubstituted $C_6$-$C_{20}$ aryl, substituted or unsubstituted $C_1$-$C_{20}$ heterocyclyl, $OR_{11}$, $C(=X_1)R_{11}$, $C(=X_1)OR_{11}$, $C(=X_1)N(R_{11})_2$, $N(R_{11})_2$, $N(R_{11})C(=X_1)R_{11}$, $SR_{11}$, $S(O)_nOR_{11}$, or $R_{11}S(O)_nR_{11}$,
wherein $R_5$, when substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, $OR_{11}$, $S(O)_nOR_{11}$, $C_6$-$C_{20}$ aryl, or $C_1$-$C_{20}$ heterocyclyl, wherein each of which is unsubstituted or substituted with $R_{11}$;
(d) Z is $Z_1$, $Z_2$, $Z_3$, $Z_4$, $Z_5$, $Z_6$, $Z_7$ or $Z_8$;

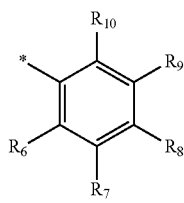

$Z_1$

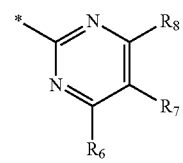

$Z_2$

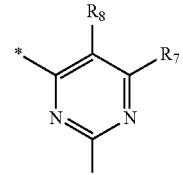

$Z_3$

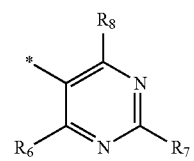

$Z_4$

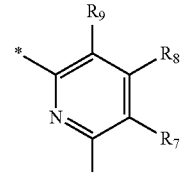

$Z_5$

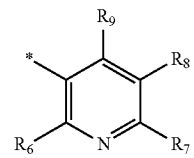

$Z_6$

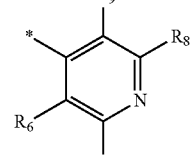

$Z_7$

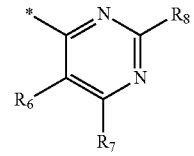

$Z_8$ (e) $R_6$ is hydrogen, F, Cl, Br, I, CN, $NO_2$, $OR_{11}$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_3$-$C_{10}$ cycloalkyl, substituted or unsubstituted $C_3$-$C_{10}$ halocycloalkyl substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, $C(=X_1)R_{11}$, $C(=X_1)OR_{11}$, $C(=X_1)N(R_1)_2$, $N(R_{11})_2$, $N(R_{11})C(=X_1)R_{11}$, $SR_{11}$, $S(O)_nOR_{11}$, or $R_{11}S(O)_nR_{11}$,
wherein $R_6$, when substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, oxo, $OR_{11}$, $S(O)_nR_{11}$, $C_6$-$C_{20}$ aryl, or $C_1$-$C_{20}$ heterocyclyl, wherein each of which is unsubstituted or substituted with $R_{11}$;

(f) $R_7$ is selected from hydrogen, F, Cl, Br, I, CN, $NO_2$, $OR_{11}$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_3$-$C_{10}$ cycloalkyl, substituted or unsubstituted $C_3$-$C_{10}$ halocycloalkyl substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, $C(=X_1)R_{11}$, $C(=X_1)OR_{11}$, $C(=X_1)N(R_{11})_2$, $N(R_{11})_2$, $N(R_{11})C(=X_1)R_{11}$, $SR_{11}$, $S(O)_nOR_{11}$, or $R_{11}S(O)_nR_{11}$, wherein $R_7$, when substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, oxo, $OR_{11}$, $S(O)_nR_{11}$, $C_6$-$C_{20}$ aryl, or $C_1$-$C_{20}$ heterocyclyl, wherein each of which is unsubstituted or substituted with $R_{11}$;

(g) $R_8$ is hydrogen, F, Cl, Br, I, CN, $NO_2$, $OR_{11}$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_3$-$C_{10}$ cycloalkyl, substituted or unsubstituted $C_3$-$C_{10}$ halocycloalkyl substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, $C(=X_1)R_{11}$, $C(=X_1)OR_{11}$, $C(=X_1)N(R_{11})_2$, $N(R_{11})_2$, $N(R_{11})C(=X_1)R_{11}$, $SR_{11}$, $S(O)_nOR_{11}$, or $R_{11}S(O)_nR_{11}$, wherein $R_8$, when substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, oxo, $OR_{11}$, $S(O)_nR_{11}$, $C_6$-$C_{20}$ aryl, or $C_1$-$C_{20}$ heterocyclyl, wherein each of which is unsubstituted or substituted with $R_{11}$;

(h) $R_9$ is hydrogen, F, Cl, Br, I, CN, $NO_2$, —$OR_{11}$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_3$-$C_{10}$ cycloalkyl, substituted or unsubstituted $C_3$-$C_{10}$ halocycloalkyl substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, $C(=X_1)R_{11}$, $C(=X_1)OR_{11}$, $C(=X_1)N(R_{11})_2$, $N(R_{11})_2$, $N(R_{11})C(=X_1)R_{11}$, $SR_{11}$, $S(O)_nOR_{11}$, or $R_{11}S(O)_nR_{11}$, wherein $R_9$, when substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, oxo, $OR_{11}$, $S(O)_nR_{11}$, $C_6$-$C_{20}$ aryl, or $C_1$-$C_{20}$ heterocyclyl, wherein each of which is unsubstituted or substituted with $R_{11}$;

(i) $R_{10}$ is selected from hydrogen, F, Cl, Br, I, CN, $NO_2$, $OR_{11}$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_3$-$C_{10}$ cycloalkyl, substituted or unsubstituted $C_3$-$C_{10}$ halocycloalkyl substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, $C(=X_1)R_{11}$, $C(=X_1)OR_{11}$, $C(=X_1)N(R_{11})_2$, $N(R_{11})_2$, $N(R_{11})C(=X_1)R_{11}$, $SR_{11}$, $S(O)_nOR_{11}$, or $R_{11}S(O)_nR_{11}$, wherein $R_{10}$, when substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, oxo, $OR_{11}$, $S(O)_nR_{11}$, $C_6$-$C_{20}$ aryl, or $C_1$-$C_{20}$ heterocyclyl, wherein each of which is unsubstituted or substituted with $R_{11}$;

(j) $R_{11}$ is hydrogen, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, substituted or unsubstituted $S(O)_nC_1$-$C_6$ alkyl, or substituted or unsubstituted $N(C_1$-$C_6$ alkyl$)_2$, wherein $R_{11}$, when substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, $OC_1$-$C_6$ alkyl, $OC_1$-$C_6$ haloalkyl, $S(O)_nC_1$-$C_6$alkyl, $S(O)_nOC_1$-$C_6$ alkyl, $C_6$-$C_{20}$ aryl, or $C_1$-$C_{20}$ heterocyclyl;

(k) $X_1$=O or S;

(l) n is 0, 1, or 2;

(m) x is 0 or 1; and (n) with the following provisos:

(1) that when Z is $Z_1$, then at least one of $R_6$ and $R_{10}$ is not hydrogen,

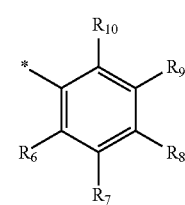

(2) that when Z is $Z_2$, then at least two of $R_6$, $R_7$ and $R_8$ are not hydrogen,

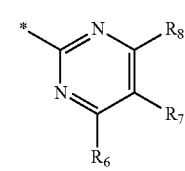

(3) that when Z is $Z_3$, then at least one of $R_7$ and $R_8$ is not hydrogen,

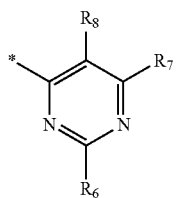

(4) that when Z is $Z_5$, then at least one of $R_8$ and $R_9$ is not hydrogen,

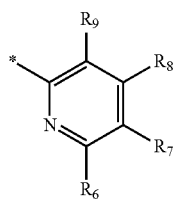

(5) that when Z is $Z_8$, then at least one of $R_6$ and $R_7$ is not hydrogen.

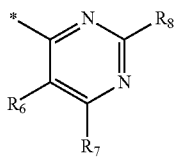

2. A composition according to claim 1, wherein $R_1$, $R_2$, and $R_4$ are H.

3. A composition according to claim 1, wherein $R_3$ is selected from H, F, Cl, Br, or I.

4. A composition according to claim 1, wherein $R_5$ is hydrogen.

5. A composition according to claim 1, wherein Z is $Z_4$, $Z_6$, or $Z_7$.

6. A composition according to claim 1, wherein Z is $Z_5$, and wherein $R_6$ and $R_7$ both simultaneously are hydrogen, or substituted or unsubstituted $C_1$-$C_6$ haloalkyl.

7. The composition of claim 1, further comprising:
(a) one or more compounds having acaricidal, algicidal, avicidal, bactericidal, fungicidal, herbicidal, insecticidal, molluscicidal, nematicidal, rodenticidal, or virucidal properties; or
(b) one or more compounds that are antifeedants, bird repellents, chemosterilants, herbicide safeners, insect attractants, insect repellents, mammal repellents, mating disrupters, plant activators, plant growth regulators, or synergists; or
(c) both (a) and (b).

8. The composition of claim 1, further comprising one or more compounds selected from: (3-ethoxypropyl)mercury bromide, 1,2-dichloropropane, 1,3-dichloropropene, 1-methylcyclopropene, 1-naphthol, 2-(octylthio)ethanol, 2,3,5-tri-iodobenzoic acid, 2,3,6-TBA, 2,3,6-TBA-dimethylammonium, 2,3,6-TBA-lithium, 2,3,6-TBA-potassium, 2,3,6-TBA-sodium, 2,4,5-T, 2,4,5-T-2-butoxypropyl, 2,4,5-T-2-ethylhexyl, 2,4,5-T-3-butoxypropyl, 2,4,5-TB, 2,4,5-T-butometyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 2iP, 2-methoxyethylmercury chloride, 2-phenylphenol, 3,4-DA, 3,4-DB, 3,4-DP, 4-aminopyridine, 4-CPA, 4-CPA-potassium, 4-CPA-sodium, 4-CPB, 4-CPP, 4-hydroxyphenethyl alcohol, 8-hydroxyquinoline sulfate, 8-phenylmercurioxyquinoline, abamectin, abscisic acid, ACC, acephate, acequinocyl, acetamiprid, acethion, acetochlor, acetophos, acetoprole, acibenzolar, acibenzolar-S-methyl, acifluorfen, acifluorfen-methyl, acifluorfen-sodium, aclonifen, acrep, acrinathrin, acrolein, acrylonitrile, acypetacs, acypetacs-copper, acypetacs-zinc, alachlor, alanycarb, albendazole, aldicarb, aldimorph, aldoxycarb, aldrin, allethrin, allicin, allidochlor, allosamidin, alloxydim, alloxydim-sodium, allyl alcohol, allyxycarb, alorac, alpha-cypermethrin, alpha-endosulfan, ametoctradin, ametridione, ametryn, amibuzin, amicarbazone, amicarthiazol, amidithion, amidoflumet, amidosulfuron, aminocarb, aminocyclopyrachlor, aminocyclopyrachlor-methyl, aminocyclopyrachlor-potassium, aminopyralid, aminopyralid-potassium, aminopyralid-tris(2-hydroxypropyl)ammonium, amiprofos-methyl, amiprophos, amisulbrom, amiton, amiton oxalate, amitraz, amitrole, ammonium sulfamate, ammonium α-naphthaleneacetate, amobam, ampropylfos, anabasine, ancymidol, anilazine, anilofos, anisuron, anthraquinone, antu, apholate, aramite, arsenous oxide, asomate, aspirin, asulam, asulam-potassium, asulam-sodium, athidathion, atraton, atrazine, aureofungin, aviglycine, aviglycine hydrochloride, azaconazole, azadirachtin, azafenidin, azamethiphos, azimsulfuron, azinphos-ethyl, azinPhos-methyl, aziprotryne, azithiram, azobenzene, azocyclotin, azothoate, azoxystrobin, bachmedesh, barban, barium hexafluorosilicate, barium polysulfide, barthrin, BCPC, beflubutamid, benalaxyl, benalaxyl-M, benazolin, benazolin-dimethylammonium, benazolin-ethyl, benazolin-potassium, bencarbazone, benclothiaz, bendiocarb, benfluralin, benfuracarb, benfuresate, benodanil, benomyl, benoxacor, benoxafos, benquinox, bensulfuron, bensulfuron-methyl, bensulide, bensultap, bentaluron, bentazone, bentazone-sodium, benthiavalicarb, benthiavalicarb-isopropyl, benthiazole, bentranil, benzadox, benzadox-ammonium, benzalkonium chloride, benzamacril, benzamacril-isobutyl, benzamorf, benzfendizone, benzipram, benzobicyclon, benzofenap, benzofluor, benzohydroxamic acid, benzoximate, benzoylprop, benzoylprop-ethyl, benzthiazuron, benzyl benzoate, benzyladenine, berberine, berberine chloride, beta-cyfluthrin, beta-cypermethrin, bethoxazin, bicyclopyrone, bifenazate, bifenox, bifenthrin, bifujunzhi, bilanafos, bilanafos-sodium, binapacryl, bingqingxiao, bioallethrin, bioethanomethrin, biopermethrin, bioresmethrin, biphenyl, bisazir, bismerthiazol, bispyribac, bispyribac-sodium, bistrifluron, bitertanol, bithionol, bixafen, blasticidin-S, borax, Bordeaux mixture, boric acid, boscalid, brassinolide, brassinolide-ethyl, brevicomin, brodifacoum, brofenvalerate, brofluthrinate, bromacil, bromacil-lithium, bromacil-sodium, bromadiolone, bromethalin, bromethrin, bromfenvinfos, bromoacetamide, bromobonil, bromobutide, bromocyclen, bromo-DDT, bromofenoxim, bromophos, bromophos-ethyl, bromopropylate, bromothalonil, bromoxynil, bromoxynil butyrate, bromoxynil heptanoate, bromoxynil octanoate, bromoxynil-potassium, brompyrazon, bromuconazole, bronopol, bucarpolate, bufencarb, buminafos, bupirimate, buprofezin, Burgundy mixture, busulfan, butacarb, butachlor, butafenacil, butamifos, butathiofos, butenachlor, butethrin, buthidazole, buthiobate, buthiuron, butocarboxim, butonate, butopyronoxyl, butoxycarboxim, butralin, butroxydim, buturon, butylamine, butylate, cacodylic acid, cadusafos, cafenstrole, calcium arsenate, calcium chlorate, calcium cyanamide, calcium polysulfide, calvinphos, cambendichlor, camphechlor, camphor, captafol, captan, carbamorph, carbanolate, carbaryl, carbasulam, carbendazim, carbendazim benzenesulfonate, carbendazim sulfite, carbetamide, carbofuran, carbon disulfide, carbon tetrachloride, carbophenothion, carbosulfan, carboxazole, carboxide, carboxin, carfentrazone, carfentrazone-ethyl, carpropamid, cartap, cartap hydrochloride, carvacrol, carvone, CDEA, cellocidin, CEPC, ceralure, Cheshunt mixture, chinomethionat, chitosan, chlobenthiazone, chlomethoxyfen, chloralose, chloramben, chloramben-ammonium, chloramben-diolamine, chloramben-methyl, chloramben-methylammonium, chloramben-sodium, chloramine phosphorus, chloramphenicol, chloraniformethan, chloranil, chloranocryl, chlorantraniliprole, chlorazifop, chlorazifop-propargyl, chlorazine, chlorbenside, chlorbenzuron, chlorbicyclen, chlorbromuron, chlorbufam, chlordane, chlordecone, chlordimeform, chlordimeform hydrochloride, chlorempenthrin, chlorethoxyfos, chloreturon, chlorfenac, chlorfenac-ammonium, chlorfenac-sodium, chlorfenapyr, chlorfenazole, chlorfenethol, chlorfenprop, chlorfenson, chlorfensulphide, chlorfenvinphos, chlorfluazuron, chlorflurazole, chlorfluren, chlorfluren-methyl, chlorflurenol, chlorflurenol-methyl, chloridazon, chlorimuron, chlorimuron-ethyl, chlormephos, chlormequat, chlormequat chloride, chlomidine, chlornitrofen, chlorobenzilate, chlorodinitronaphthalenes, chloroform, chloromebuform, chloromethiuron, chloroneb, chlorophacinone, chlorophacinone-sodium, chloropicrin, chloropon, chloropropylate, chlorothalonil, chlorotoluron, chloroxuron, chloroxynil, chlorphonium, chlorphonium chloride, chlorphoxim, chlorprazophos, chlorprocarb, chlorpropham, chlorpyrifos, chlorpyrifos-methyl, chlorquinox, chlorsulfuron, chlorthal, chlorthal-dimethyl, chlorthal-monomethyl, chlorthiamid, chlorthiophos, chlozolinate, choline chloride, chromafenozide, cinerin I, cinerin II, cinerins, cinidon-ethyl, cinmethylin, cinosulfuron, ciobutide, cisanilide, cismethrin, clethodim, climbazole, cliodinate, clodinafop, clodinafop-propargyl, cloethocarb, clofencet, clofencet-potassium, clofentezine, clofibric acid, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloquintocet, cloquintocet-mexyl, cloransulam, cloransulam-methyl, closantel, clothianidin, clotrimazole, cloxyfonac, cloxyfonac-sodium, CMA, codlelure, colophonate, copper acetate, copper acetoarsenite, copper arsenate, copper carbonate, basic, copper hydroxide, copper naphthenate, copper oleate, copper oxychloride, copper silicate, copper sulfate, copper zinc chromate, coumachlor, coumafuryl, coumaphos, coumatetralyl, coumithoate, coumoxystrobin, CPMC, CPMF, CPPC, credazine, cresol, crimidine, crotamiton, crotoxyphos, crufomate, cryolite, cue-lure, cufraneb, cumyluron, cuprobam, cuprous oxide, curcumenol, cyanamide, cyanatryn, cyanazine, cyanofenphos, cyanophos, cyanthoate, cyantraniliprole, cyazofamid, cybutryne, cyclafuramid, cyclanilide, cyclethrin, cycloate, cycloheximide, cycloprate, cycloprothrin, cyclosulfamuron, cycloxydim, cycluron, cyenopyrafen, cyflufenamid, cyflumetofen, cyfluthrin, cyhalofop, cyhalofop-butyl, cyhalothrin, cyhexatin, cymiazole, cymiazole hydrochloride, cymoxanil, cyometrinil, cypendazole, cypermethrin, cyperquat, cyperquat chloride, cyphenothrin, cyprazine, cyprazole, cyproconazole, cyprodinil, cyprofuram, cypromid, cyprosulfamide, cyromazine, cythioate, daimuron, dalapon, dalapon-calcium, dalapon-magnesium, dalapon-sodium, daminozide, dayoutong, dazomet, dazomet-sodium, DBCP, d-camphor, DCIP, DCPTA, DDT, debacarb, decafentin, decarbofuran, dehydroacetic acid, delachlor, deltamethrin, demephion, demephion-O, demephion-S, demeton, demeton-methyl, demeton-O, demeton-O-methyl, demeton-S, demeton-S-methyl, demeton-S-methylsulphon, desmedipham, desmetryn, d-fanshiluquebingjuzhi, diafenthiuron, dialifos, di-allate, diamidafos, diatomaceous earth, diazinon, dibutyl phthalate, dibutyl succinate, dicamba, dicamba-diglycolamine, dicamba-dimethylammonium, dicamba-diolamine, dicamba-isopropylammonium, dicamba-methyl, dicamba-olamine, dicamba-potassium, dicamba-sodium, dicamba-trolamine, dicapthon, dichlobenil, dichlofenthion, dichlofluanid, dichlone, dichloralurea, dichlorbenzuron, dichlorflurenol, dichlorflurenol-methyl, dichlormate, dichlormid, dichlorophen, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-2-ethylhexyl, dichlorprop-P-dimethylammonium, dichlorprop-potassium, dichlorprop-sodium, dichlorvos, dichlozoline, diclobutrazol, diclocymet, diclofop, diclofop-methyl, diclomezine, diclomezine-sodium, dicloran, diclosulam, dicofol, dicoumarol, dicresyl, dicrotophos, dicyclanil, dicyclonon, dieldrin, dienochlor, diethamquat, diethamquat dichloride, diethatyl, diethatyl-ethyl, diethofencarb, diethyl pyrocarbonate, diethyltoluamide, difenacoum, difenoconazole, difenopenten, difenopenten-ethyl, difenoxuron, difenzoquat, difenzoquat metilsulfate, difethialone, diflovidazin, diflubenzuron, diflufenican, diflufenzopyr, diflufenzopyr-sodium, diflumetorim, dikegulac, dikegulac-sodium, dilor, dimatif, dimefluthrin, dimefox, dimefuron, dimepiperate, dimetachlone, dimetan, dimethacarb, dimethachlor, dimethametryn, dimethenamid, dimethenamid-P, dimethipin, dimethirimol, dimethoate, dimethomorph, dimethrin, dimethyl carbate, dimethyl phthalate, dimethylvinphos, dimetilan, dimexano, dimidazon, dimoxystrobin, dinex, dinex-diclexine, dingjunezuo, diniconazole, diniconazole-M, dinitramine, dinobuton, dinocap, dinocap-4, dinocap-6, dinocton, dinofenate, dinopenten, dinoprop, dinosaur, dinoseb, dinoseb acetate, dinoseb-ammonium, dinoseb-diolamine, dinoseb-sodium, dinoseb-trolamine, dinosulfon, dinotefuran, dinoterb, dinoterb acetate, dinoterbon, diofenolan, dioxabenzofos, dioxacarb, dioxathion, diphacinone, diphacinone-sodium, diphenamid, diphenyl sulfone, diphenylamine, dipropalin, dipropetryn, dipyrithione, diquat, diquat dibromide, disparlure, disul, disulfiram, disulfoton, disul-sodium, ditalimfos, dithianon, dithicrofos, dithioether, dithiopyr, diuron, d-limonene, DMPA, DNOC, DNOC-ammonium, DNOC-potassium, DNOC-sodium, dodemorph, dodemorph acetate, dodemorph benzoate, dodicin, dodicin hydrochloride, dodicin-sodium, dodine, dofenapyn, dominicalure, doramectin, drazoxolon, DSMA, dufulin, EBEP, EBP, ecdysterone, edifenphos, eglinazine, eglinazine-ethyl, emamectin, emamectin benzoate, EMPC, empenthrin, endosulfan, endothal, endothal-diammonium, endothal-dipotassium, endothal-disodium, endothion, endrin, enestroburin, EPN, epocholeone, epofenonane, epoxiconazole, eprinomectin, epronaz, EPTC, erbon, ergocalciferol, erlujixiancaoan, esdépalléthrine, esfenvalerate, esprocarb, etacelasil, etaconazole, etaphos, etem, ethaboxam, ethachlor, ethafluralin, ethametsulfuron, ethametsulfuron-methyl, ethaprochlor, ethephon, ethidimuron, ethiofencarb, ethiolate, ethion, ethiozin, ethiprole, ethirimol, ethoate-methyl, ethofumesate, ethohexadiol, ethoprophos, ethoxyfen, ethoxyfenethyl, ethoxyquin, ethoxysulfuron, ethychlozate, ethyl formate, ethyl α-naphthaleneacetate, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, etnipromid, etobenzanid, etofenprox, etoxazole, etridiazole, etrimfos, eugenol, EXD, famoxadone, famphur, fenamidone, fenaminosulf, fenamiphos, fenapanil, fenarimol, fenasulam, fenazaflor, fenazaquin, fenbuconazole, fenbutatin oxide, fenchlorazole, fenchlorazole-ethyl, fenchlorphos, fenclorim, fenethacarb, fenfluthrin, fenfuram, fenhexamid, fenitropan, fenitrothion, fenjuntong, fenobucarb, fenoprop, fenoprop-3-butoxypropyl, fenoprop-butometyl, fenoprop-butotyl, fenoprop-butyl, fenoprop-isoctyl, fenoprop-methyl, fenoprop-potassium, fenothiocarb, fenoxacrim, fenoxanil, fenoxaprop, fenoxaprop-ethyl, fenoxaprop-P, fenoxaprop-P-ethyl, fenoxasulfone, fenoxycarb, fenpiclonil, fenpirithrin, fenpropathrin, fenpropidin, fenpropimorph, fenpyrazamine, fenpyroximate, fenridazon, fenridazon-potassium, fenridazon-propyl, fenson, fensulfothion, fenteracol, fenthiaprop, fenthiaprop-ethyl, fenthion, fenthion-ethyl, fentin, fentin acetate, fentin chloride, fentin hydroxide, fentrazamide, fentrifanil, fenuron, fenuron TCA, fenvalerate, ferbam, ferimzone, ferrous sulfate, fipronil, flamprop, flamprop-isopropyl, flamprop-M, flamprop-methyl, flamprop-M-isopropyl, flamprop-M-methyl, flazasulfuron, flocoumafen, flometoquin, flonicamid, florasulam, fluacrypyrim, fluazifop, fluazifop-butyl, fluazifop-methyl, fluazifop-P, fluazifop-P-butyl, fluazinam, fluazolate, fluazuron, flubendiamide, flubenzimine, flucarbazone, flucarbazone-sodium, flucetosulfuron, fluchloralin, flucofuron, flucycloxuron, flucythrinate, fludioxonil, fluenetil, fluensulfone, flufenacet, flufenerim, flufenican, flufenoxuron, flufenprox, flufenpyr, flufenpyr-ethyl, flufiprole, flumethrin, flumetover, flumetralin, flumetsulam, flumezin, flumiclorac, flumiclorac-pentyl, flumioxazin, flumipropyn, flumorph, fluometuron, fluopicolide, fluopyram, fluorbenside, fluoridamid, fluoroacetamide, fluorodifen, fluoroglycofen, fluoroglycofen-ethyl, fluoroimide, fluoromidine, fluoronitrofen, fluothiuron, fluotrimazole, fluoxastrobin, flupoxam, flupropacil, flupropadine, flupropanate, flupropanate-sodium, flupyradifurone, flupyrsulfuron, flupyrsulfuron-methyl, flupyrsulfuron-methyl-sodium, fluquinconazole, flurazole, flurenol, flurenol-butyl, flurenol-methyl, fluridone, flurochloridone, fluroxypyr, fluroxypyr-butometyl, fluroxypyr-meptyl, flurprimidol, flursulamid, flurtamone, flusilazole, flusulfamide, fluthiacet, fluthiacet-methyl, flutianil, flutolanil, flutriafol, fluvalinate, fluxapyroxad, fluxofenim, folpet, fomesafen, fomesafen-sodium, fonofos, foramsulfuron, forchlorfenuron, formaldehyde, formetanate, formetanate hydrochloride, formothion, formparanate, formparanate hydrochloride, fosamine, fosamine-ammonium, fosetyl, fosetyl-aluminium, fosmethilan, fospirate, fosthiazate, fosthietan, frontalin, fuberidazole, fucaojing, fucaomi, funaihecaoling, fuphenthiourea, furalane, furalaxyl, furamethrin, furametpyr, furathiocarb, furcarbanil, furconazole, furconazole-cis, furethrin, furfural, furilazole, furmecyclox, furophanate, furyloxyfen, gamma-cyhalothrin, gamma-HCH, genit, gibberellic acid, gibberellins, gliftor, glufosinate, glufosinate-ammonium, glufosinate-P, glufosinate-P-ammonium, glufosinate-P-sodium, glyodin, glyoxime, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, glyphosine, gossyplure, grandlure, griseofulvin, guazatine, guazatine acetates, halacrinate, halfenprox, halofenozide, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, HCH, hemel, hempa, HEOD, heptachlor, heptenophos, heptopargil, heterophos, hexachloroacetone, hexachlorobenzene, hexachlorobutadiene, hexachlorophene, hexaconazole, hexaflumuron, hexaflurate, hexalure, hexamide, hexazinone, hexylthiofos, hexythiazox, HHDN, holosulf, huancaiwo, huangcaoling, huanjunzuo, hydramethylnon, hydrargaphen, hydrated lime, hydrogen cyanide, hydroprene, hymexazol, hyquincarb, IAA, IBA, icaridin, imazalil, imazalil nitrate, imazalil sulfate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, imibenconazole, imicyafos, imidacloprid, imidaclothiz, iminoctadine, iminoctadine triacetate, iminoctadine trialbesilate, imiprothrin, inabenfide, indanofan, indaziflam, indoxacarb, inezin, iodobonil, iodocarb, iodomethane, iodosulfuron, iodosulfuron-methyl, iodosulfuron-methyl-sodium, iofensulfuron, iofensulfuron-sodium, ioxynil, ioxynil octanoate, ioxynil-lithium, ioxynil-sodium, ipazine, ipconazole, ipfencarbazone, iprobenfos, iprodione, iprovalicarb, iprymidam, ipsdienol, ipsenol, IPSP, isamidofos, isazofos, isobenzan, isocarbamid, isocarbophos, isocil, isodrin, isofenphos, isofenphos-methyl, isolan, isomethiozin, isonoruron, isopolinate, isoprocarb, isopropalin, isoprothiolane, isoproturon, isopyrazam, isopyrimol, isothioate, isotianil, isouron, isovaledione, isoxaben, isoxachlortole, isoxadifen, isoxadifen-ethyl, isoxaflutole, isoxapyrifop, isoxathion, ivermectin, izopamfos, japonilure, japothrins, jasmolin I, jasmolin II, jasmonic acid, jiahuangchongzong, jiajizengxiaolin, jiaxiangjunzhi, jiecaowan, jiecaoxi, jodfenphos, juvenile hormone I, juvenile hormone II, juvenile hormone III, kadethrin, karbutilate, karetazan, karetazan-potassium, kasugamycin, kasugamycin hydrochloride, kejunlin, kelevan, ketospiradox, ketospiradox-potassium, kinetin, kinoprene, kresoxim-methyl, kuicaoxi, lactofen, lambda-cyhalothrin, latilure, lead arsenate, lenacil, lepimectin, leptophos, lindane, lineatin, linuron, lirimfos, litlure, looplure, lufenuron, lvdingjunzhi, lvxiancaolin, lythidathion, MAA, malathion, maleic hydrazide, malonoben, maltodextrin, MAMA, mancopper, mancozeb, mandipropamid, maneb, matrine, mazidox, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mebenil, mecarbam, mecarbinzid, mecarphon, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-2-ethylhexyl, mecoprop-P-climethylammonium, mecoprop-P-isobutyl, mecoprop-potassium, mecoprop-P-potassium, mecoprop-sodium, mecoprop-trolamine, medimeform, medinoterb, medinoterb acetate, medlure, mefenacet, mefenpyr, mefenpyr-diethyl, mefluidide, mefluidide-diolamine, mefluidide-potassium, megatomoic acid, menazon, mepanipyrim, meperfluthrin, mephenate, mephosfolan, mepiquat, mepiquat chloride, mepiquat pentaborate, mepronil, meptyldinocap, mercuric chloride, mercuric oxide, mercurous chloride, merphos, mesoprazine, mesosulfuron, mesosulfuron-methyl, mesotrione, mesulfen, mesulfenfos, metaflumizone, metalaxyl, metalaxyl-M, metaldehyde, metam, metam-ammonium, metamifop, metamitron, metam-potassium, metam-sodium, metazachlor, metazosulfuron, metazoxolon, metconazole, metepa, metflurazon, methabenzthiazuron, methacrifos, methalpropalin, methamidophos, methasulfocarb, methazole, methfuroxam, methidathion, methiobencarb, methiocarb, methiopyrisulfuron, methiotepa, methiozolin, methiuron, methocrotophos, methometon, methomyl, methoprene, methoprotryne, methoquin-butyl, methothrin, methoxychlor, methoxyfenozide, methoxyphenone, methyl apholate, methyl bromide, methyl eugenol, methyl iodide, methyl isothiocyanate, methylacetophos, methylchloroform, methyldymron, methylene chloride, methylmercury benzoate, methylmercury dicyandiamide, methylmercury pentachlorophenoxide, methylneodecanamide, metiram, metobenzuron, metobromuron, metofluthrin, metolachlor, metolcarb, metominostrobin, metosulam, metoxadiazone, metoxuron, metrafenone, metribuzin, metsulfovax, metsulfuron, metsulfuron-methyl, mevinphos, mexacarbate, mieshuan, milbemectin, milbemycin oxime, milneb, mipafox, mirex, MNAF, moguchun, molinate, molosultap, monalide, monisouron, monochloroacetic acid, monocrotophos, monolinuron, monosulfuron, monosulfuron-ester, monuron, monuron TCA, morfamquat, morfamquat dichloride, moroxydine, moroxydine hydrochloride, morphothion, morzid, moxidectin, MSMA, muscalure, myclobutanil, myclozolin, N-(ethylmercury)-p-toluenesulphonanilide, nabam, naftalofos, naled, naphthalene, naphthaleneacetamide, naphthalic anhydride, naphthoxyacetic acids, naproanilide, napropamide, naptalam, naptalam-sodium, natamycin, neburon, niclosamide, niclosamide-olamine, nicosulfuron, nicotine, nifluridide, nipyraclofen, nitenpyram, nithiazine, nitralin, nitrapyrin, nitrilacarb, nitrofen, nitrofluorfen, nitrostyrene, nitrothal-isopropyl, norbormide, norflurazon, nornicotine, noruron, novaluron, novifluminron, nuarimol, OCH, octachlorodipropyl ether, octhilinone, ofurace, omethoate, orbencarb, orfralure, ortho-dichlorobenzene, orthosulfamuron, oryctalure, orysastrobin, oryzalin, osthol, ostramone, oxabetrinil, oxadiargyl, oxadiazon, oxadixyl, oxamate, oxamyl, oxapyrazon, oxapyrazon-dimolamine, oxapyrazon-sodium, oxasulfuron, oxaziclomefone, oxine-copper, oxolinic acid, oxpoconazole, oxpoconazole fumarate, oxycarboxin, oxydemeton-methyl, oxydeprofos, oxydisulfoton, oxyfluorfen, oxymatrine, oxytetracycline, oxytetracycline hydrochloride, paclobutrazol, paichongding, para-dichlorobenzene, parafluron, paraquat, paraquat dichloride, paraquat dimetilsulfate, parathion, parathion-methyl, parinol, pebulate, pefurazoate, pelargonic acid, penconazole, pencycuron, pendimethalin, penflufen, penfluron, penoxsulam, pentachlorophenol, pentanochlor, penthiopyrad, pentmethrin, pentoxazone, perfluidone, permethrin, pethoxamid, phenamacril, phenazine oxide, phenisopham, phenkapton, phenmedipham, phenmedipham-ethyl, phenobenzuron, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosdiphen, phosfolan, phosfolan-methyl, phosglycin, phosmet, phosnichlor, phosphamidon, phosphine, phosphocarb, phosphorus, phostin, phoxim, phoxim-methyl, phthalide, picloram, picloram-2-ethylhexyl, picloram-isoctyl, picloram-methyl, picloram-olamine, picloram-potassium, picloram-triethylammonium, picloram-tris(2-hydroxypropyl)ammonium, picolinafen, picoxystrobin, pindone, pindone-sodium, pinoxaden, piperalin, piperonyl butoxide, piperonyl cyclonene, piperophos, piproctanyl, piproctanyl bromide, piprotal, pirimetaphos, pirimicarb, pirimioxyphos, pirimiphos-ethyl, pirimiphos-methyl, plifenate, polycarbamate, polyoxins, polyoxorim, polyoxorim-zinc, polythialan, potassium arsenite, potassium azide, potassium cyanate, potassium gibberellate, potassium naphthenate, potassium polysulfide, potassium thiocyanate, potassium α-naphthaleneacetate, pp'-DDT, prallethrin, precocene I, precocene II, precocene III, pretilachlor, primidophos, primisulfuron, primisulfuron-methyl, probenazole, prochloraz, prochloraz-manganese, proclonol, procyazine, procymidone, prodiamine, profenofos, profluazol, profluralin, profluthrin, profoxydim, proglinazine, proglinazine-ethyl, prohexadione, prohexadione-calcium, prohydrojasmon, promacyl, promecarb, prometon, prometryn, promurit, propachlor, propamidine, propamidine dihydrochloride, propamocarb, propamocarb hydrochloride, propanil, propaphos, propaquizafop, propargite, proparthrin, propazine, propetamphos, propham, propiconazole, propineb, propisochlor, propoxur, propoxycarbazone, propoxycarbazone-sodium, propyl isome, propyrisulfuron, propyzamide, proquinazid, prosuler, prosulfalin, prosulfocarb, prosulfuron, prothidathion, prothiocarb, prothiocarb hydrochloride, prothioconazole, prothiofos, prothoate, protrifenbute, proxan, proxan-sodium, prynachlor, pydanon, pymetrozine, pyracarbolid, pyraclofos, pyraclonil, pyraclostrobin, pyraflufen, pyraflufen-ethyl, pyrafluprole, pyramat, pyrametostrobin, pyraoxystrobin, pyrasulfotole, pyrazolynate, pyrazophos, pyrazosulfuron, pyrazosulfuron-ethyl, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridafol, pyridalyl, pyridaphenthion, pyridate, pyridinitril, pyrifenox, pyrifluquinazon, pyriftalid, pyrimethanil, pyrimidifen, pyriminobac, pyriminobac-methyl, pyrimisulfan, pyrimitate, pyrinuron, pyriofenone, pyriprole, pyripropanol, pyriproxyfen, pyrithiobac, pyrithiobac-sodium, pyrolan, pyroquilon, pyroxasulfone, pyroxsulam, pyroxychlor, pyroxyfur, quassia, quinacetol, quinacetol sulfate, quinalphos, quinalphos-methyl, quinazamid, quinclorac, quinconazole, quinmerac, quinoclamine, quinonamid, quinothion, quinoxyfen, quintiofos, quintozene, quizalofop, quizalofop-ethyl, quizalofop-P, quizalofop-P-ethyl, quizalofop-P-tefuryl, quwenzhi, quyingding, rabenzazole, rafoxanide, rebemide, resmethrin, rhodethanil, rhodojaponin-III, ribavirin, rimsulfuron, rotenone, ryania, saflufenacil, saijunmao, saisentong, salicylanilide, sanguinarine, santonin, schradan, scilliroside, sebuthylazine, secbumeton, sedaxane, selamectin, semiamitraz, semiamitraz chloride, sesamex, sesamolin, sethoxydim, shuangjiaancaolin, siduron, siglure, silafluofen, silatrane, silica gel, silthiofam, simazine, simeconazole, simeton, simetryn, sintofen, SMA, S-metolachlor, sodium arsenite, sodium azide, sodium chlorate, sodium fluoride, sodium fluoroacetate, sodium hexafluorosilicate, sodium naphthenate, sodium orthophenylphenoxide, sodium pentachlorophenoxide, sodium polysulfide, sodium thiocyanate, sodium α-naphthaleneacetate, sophamide, spinetoram, spinosad, spirodiclofen, spiromesifen, spirotetramat, spiroxamine, streptomycin, streptomycin sesquisulfate, strychnine, sulcatol, sulcofuron, sulcofuron-sodium, sulcotrione, sulfallate, sulfentrazone, sulfiram, sulfluramid, sulfometuron, sulfometuron-methyl, sulfosulfuron, sulfotep, sulfoxaflor, sulfoxide, sulfoxime, sulfur, sulfuric acid, sulfuryl fluoride, sulglycapin, sulprofos, sultropen, swep, tau-fluvalinate, tavron, tazimcarb, TCA, TCA-ammonium, TCA-calcium, TCA-ethadyl, TCA-magnesium, TCA-sodium, TDE, tebuconazole, tebufenozide, tebufenpyrad, tebufloquin, tebupirimfos, tebutam, tebuthiuron, tecloftalam, tecnazene, tecoram, teflubenzuron, tefluthrin, tefuryltrione, tembotrione, temephos, tepa, TEPP, tepraloxydim, terallethrin, terbacil, terbucarb, terbuchlor, terbufos, terbumeton, terbuthylazine, terbutryn, tetcyclacis, tetrachloroethane, tetrachlorvinphos, tetraconazole, tetradifon, tetrafluron, tetramethrin, tetramethylfluthrin, tetramine, tetranactin, tetrasul, thallium sulfate, thenylchlor, theta-cypermethrin, thiabendazole, thiacloprid, thiadifluor, thiamethoxam, thiapronil, thiazafluron, thiazopyr, thicrofos, thicyofen, thidiazimin, thidiazuron, thiencarbazone, thiencarbazone-methyl, thifensulfuron, thifensulfuron-methyl, thifluzamide, thiobencarb, thiocarboxime, thiochlorfenphim, thiocyclam, thiocyclam hydrochloride, thiocyclam oxalate, thiodiazole-copper, thiodicarb, thiofanox, thiofluoximate, thiohempa, thiomersal, thiometon, thionazin, thiophanate, thiophanate-methyl, thioquinox, thiosemicarbazide, thiosultap, thiosultap-diammonium, thiosultap-disodium, thiosultap-monosodium, thiotepa, thiram, thuringiensin, tiadinil, tiaojiean, tiocarbazil, tioclorim, tioxymid, tirpate, tolclofos-methyl, tolfenpyrad, tolylfluanid, tolylmercury acetate, topramezone, tralkoxydim, tralocythrin, tralomethrin, tralopyril, transfluthrin, transpermethrin, tretamine, triacontanol, triadimefon, triadimenol, triafamone, tri-allate, triamiphos, triapenthenol, triarathene, triarimol, triasulfuron, triazamate, triazbutil, triaziflam, triazophos, triazoxide, tribenuron, tribenuron-methyl, tribufos, tributyltin oxide, tricamba, trichlamide, trichlorfon, trichlormetaphos-3, trichloronat, triclopyr, triclopyr-butotyl, triclopyr-ethyl, triclopyr-triethylammonium, tricyclazole, tridemorph, tridiphane, trietazine, trifenmorph, trifenofos, trifloxystrobin, trifloxysulfuron, trifloxysulfuron-sodium, triflumizole, triflumuron, trifluralin, triflusulfuron, triflusulfuron-methyl, trifop, trifop-methyl, trifopsime, triforine, trihydroxytriazine, trimedlure, trimethacarb, trimeturon, trinexapac, trinexapac-ethyl, triprene, tripropindan, triptolide, tritac, triticonazole, tritosulfuron, trunc-call, uniconazole, uniconazole-P, urbacide, uredepa, valerate, validamycin, valifenalate, valone, vamidothion, vangard, vaniliprole, vernolate, vinclozolin, warfarin, warfarin-potassium, warfarin-sodium, xiaochongliulin, xinjunan, xiwojunan, XMC, xylachlor, xylenols, xylylcarb, yishijing, zarilamid, zeatin, zengxiaoan, zeta-cypermethrin, zinc naphthenate, zinc phosphide, zinc thiazole, zineb, ziram, zolaprofos, zoxamide, zuomihuanglong, α-chlorohydrin, α-ecdysone, α-multistriatin, and α-naphthaleneacetic acid.

9. The composition of claim 1, further comprising an agriculturally acceptable carrier.

10. The composition of claim 1, wherein the pyridine triazole compound is in the form of a pesticidally acceptable acid addition salt.

11. The composition of claim 1, wherein the pyridine triazole compound is in the form of a salt derivative.

12. The composition of claim 1, wherein the pyridine triazole compound is in the form a hydrate.

13. The composition of claim 1, wherein the pyridine triazole compound is a resolved stereoisomer.

14. The composition of claim 1, wherein the pyridine triazole compound is in the form a crystal polymorph.

15. The composition of claim 1, wherein the pyridine triazole compound comprises a $^2H$ in place of $^1H$.

16. The composition of claim 1, wherein the pyridine triazole compound comprises a $^{13}C$ in place of a $^{12}C$.

17. The composition of claim 1, further comprising a biopesticide.

18. The composition of claim 1, further comprising one or more of the following compounds:
(a) 3-(4-chloro-2,6-dimethylphenyl)-4-hydroxy-8-oxa-1-azaspiro[4,5]dec-3-en-2-one;
(b) 3-(4'-chloro-2,4-dimethyl[1,1'-biphenyl]-3-yl)-4-hydroxy-8-oxa-1-azaspiro[4,5]dec-3-en-2-one;
(c) 4-[[(6-chloro-3-pyridinyl)methyl]methylamino]-2(5H)-furanone;
(d) 4-[[(6-chloro-3-pyridinyl)methyl]cyclopropylamino]-2(5H)-furanone;
(e) 3-chloro-N2-[(1S)-1-methyl-2-(methylsulfonyl)ethyl]-N1-[2-methyl-4-[1,2,2,2-tetrafluoro-1-(trifluoromethyl)ethyl]phenyl]-1,2-benzenedicarboxamide;
(f) 2-cyano-N-ethyl-4-fluoro-3-methoxy-benenesulfonamide;
(g) 2-cyano-N-ethyl-3-methoxy-benzenesulfonamide;
(h) 2-cyano-3-difluoromethoxy-N-ethyl-4-fluoro-benzenesulfonamide;
(i) 2-cyano-3-fluoromethoxy-N-ethyl-benzenesulfonamide;
(j) 2-cyano-6-fluoro-3-methoxy-N,N-dimethyl-benzenesulfonamide;
(k) 2-cyano-N-ethyl-6-fluoro-3-methoxy-N-methyl-benzenesulfonamide;
(l) 2-cyano-3-difluoromethoxy-N,N-dimethylbenzenesulfon-amide;
(m) 3-(difluoromethyl)-N-[2-(3,3-dimethylbutyl)phenyl]-1-methyl-1H-pyrazole-4-carboxamide;
(n) N-ethyl-2,2-dimethylpropionamide-2-(2,6-dichloro-α,α,α-trifluoro-p-tolyl) hydrazone;
(o) N-ethyl-2,2-dichloro-1-methylcyclopropane-carboxamide-2-(2,6-dichloro-α,α,α-trifluoro-p-tolyl) hydrazone nicotine;
(p) O-{(E-)-[2-(4-chloro-phenyl)-2-cyano-1-(2-trifluoromethylphenyl)-vinyl]}S-methyl thiocarbonate;
(q) (E)-N1-[(2-chloro-1,3-thiazol-5-ylmethyl)]-N2-cyano-N1-methylacetamidine;
(r) 1-(6-chloropyridin-3-ylmethyl)-7-methyl-8-nitro-1,2,3,5,6,7-hexahydro-imidazo[1,2-a]pyridin-5-ol;
(s) 4-[4-chlorophenyl-(2-butylidine-hydrazono)methyl)] phenyl mesylate; and
(t) N-Ethyl-2,2-dichloro-1-methylcyclopropanecarboxamide-2-(2,6-dichloro-α,α,α-trifluoro-p-tolyl)hydrazone.

19. The composition of claim 1, further comprising a compound having one or more of the following modes of action: acetylcholinesterase inhibitor; sodium channel modulator; chitin biosynthesis inhibitor; GABA and glutamate-gated chloride channel antagonist; GABA and glutamate-gated chloride channel agonist; acetylcholine receptor agonist; acetylcholine receptor antagonist; MET I inhibitor; Mg-stimulated ATPase inhibitor; nicotinic acetylcholine receptor; Midgut membrane disrupter; oxidative phosphorylation disrupter, and ryanodine receptor (RyRs).

20. The composition of claim 1, further comprising a seed.

21. The composition of claim 1, further comprising a seed that has been genetically modified to express one or more specialized traits.

22. The composition of to claim 1, wherein the composition is encapsulated inside, or placed on the surface of, a capsule.

23. The composition of claim 1, wherein the composition is encapsulated inside, or placed on the surface of, a capsule, wherein the capsule has a diameter of about 100-900 nanometers or about 10 -900 microns.

24. A process comprising applying a composition of claim 1, to an area to control a pest, in an amount sufficient to control such pest.

25. The process of claim 24, wherein the pest is selected from beetles, earwigs, cockroaches, flies. aphids, scales, whiteflies, leafhoppers, ants, wasps, termites, moths, butterflies, lice, grasshoppers, locusts, crickets, fleas, thrips, bristletails, mites, ticks, nematodes, and symphylans.

26. The process of claim 24, wherein the pest is from the Phyla Nematoda or Arthropoda.

27. The process of claim 24, wherein the pest is from the Subphyla Chelicerata, Myriapoda, or Hexapoda.

28. The process of claim 24, wherein the pest is from the Class of Arachnida, Symphyla, or Insecta.

29. The process of claim 24, wherein the pest is from the Order Anoplura, Order Coleoptera, Order Dermaptera, Order Blattaria, Order Diptera, Order Hemiptera, Order Hymenoptera, Order Isoptera, Order Lepidoptera, Order Mallophaga, Order Orthoptera, Order Siphonaptera, Order Thysanoptera, Order Thysanura, Order Acarina, or Order Symphyla.

30. The process of claim 24, wherein the pest is MYZUPE or BEMITA.

31. The process of claim 24, wherein an amount of the composition is from about 0.01 grams per hectare to about 5000 grams per hectare.

32. The process of claim 24, wherein an amount of the composition is from about 0.1 grams per hectare to about 500 grams per hectare.

33. The process of claim 24, wherein an amount of the composition is from about 1 gram per hectare to about 50 grams per hectare.

34. The process of claim 24, wherein the area is an area where apples, corn, cotton, soybeans, canola, wheat, rice, sorghum, barley, oats, potatoes, oranges, alfalfa, lettuce, strawberries, tomatoes, peppers, crucifers, pears, tobacco, almonds, sugar beets, or beans, are growing, or the seeds thereof are going to be planted.

35. The process of claim 24, further comprising applying the composition to a genetically modified plant that has been genetically modified to express one or more specialized traits.

36. The process of claim 24, where the composition further comprises ammonium sulfate.

37. A method of preparing a pyridine triazole compounds of formula I, comprising:
reacting a pyridine triazole compounds of formula 1-1 with an aryl or heterocyclic halide of formula 1-2,

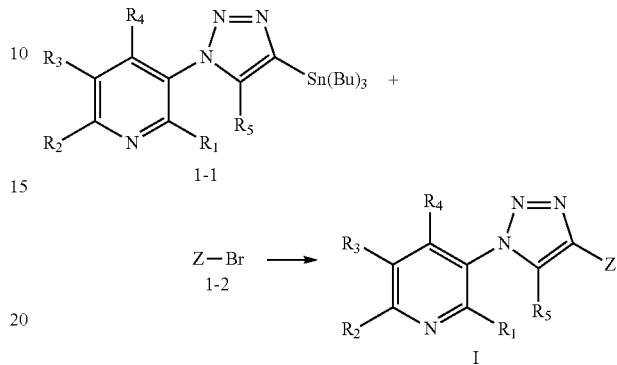

wherein $R_1$, $R_2$, $R_3$, $R_4$, $R_5$, Z, and x are defined as in claim 1.

38. A method of preparing a pyridine triazole compounds of formula I, comprising:
reacting 4-iodo-triazole compounds of formula 2-1 with an aryl or heterocyclic boronic acid compounds of formula 2-2,

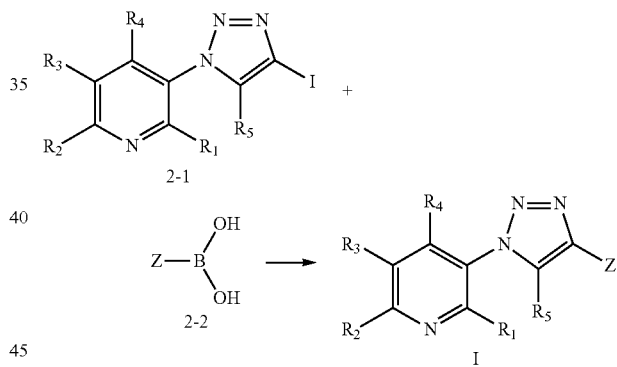

wherein $R_1$, $R_2$, $R_3$, $R_4$, $R_5$, Z, and x are defined as in claim 1.

* * * * *